(12) United States Patent
Sato

(10) Patent No.: US 12,286,650 B2
(45) Date of Patent: Apr. 29, 2025

(54) POLYPEPTIDE SET TO BE USED IN LIGHT DEPENDENT GENE RECOMBINATION

(71) Applicant: The University of Tokyo, Tokyo (JP)

(72) Inventor: Moritoshi Sato, Tokyo (JP)

(73) Assignee: The University of Tokyo, Tokyo (JP)

( * ) Notice: Subject to any disclaimer, the term of this patent is extended or adjusted under 35 U.S.C. 154(b) by 1102 days.

(21) Appl. No.: 16/604,351

(22) PCT Filed: Apr. 10, 2018

(86) PCT No.: PCT/JP2018/015136
§ 371 (c)(1),
(2) Date: Jan. 30, 2020

(87) PCT Pub. No.: WO2018/190348
PCT Pub. Date: Oct. 18, 2018

(65) Prior Publication Data
US 2020/0157514 A1    May 21, 2020

(30) Foreign Application Priority Data
Apr. 10, 2017   (JP) ................. 2017-077804

(51) Int. Cl.
| | | |
|---|---|---|
| C07K 14/37 | (2006.01) | |
| A01K 67/0275 | (2024.01) | |
| A61K 38/43 | (2006.01) | |
| C07K 19/00 | (2006.01) | |
| C12N 9/00 | (2006.01) | |
| C12N 9/12 | (2006.01) | |
| C12N 15/62 | (2006.01) | |
| C12N 15/63 | (2006.01) | |
| C12N 15/85 | (2006.01) | |

(52) U.S. Cl.
CPC ........ *C12N 9/1241* (2013.01); *A01K 67/0275* (2013.01); *A61K 38/43* (2013.01); *C07K 14/37* (2013.01); *C07K 19/00* (2013.01); *C12N 9/00* (2013.01); *C12N 15/62* (2013.01); *C12N 15/63* (2013.01); *C12N 15/85* (2013.01); *A01K 2217/07* (2013.01); *A01K 2227/105* (2013.01); *C07K 2319/00* (2013.01); *C07K 2319/61* (2013.01); *C12N 2800/30* (2013.01); *Y10S 930/22* (2013.01)

(58) Field of Classification Search
CPC .... C07K 14/37; C07K 19/00; C07K 2319/00; C07K 2319/61; C12N 15/62; C12N 15/63; C12N 15/85; C12N 9/00; C12N 2800/30
See application file for complete search history.

(56) References Cited

U.S. PATENT DOCUMENTS

| | | | | |
|---|---|---|---|---|
| 9,839,698 | B2 * | 12/2017 | Yang | A61K 48/0083 |
| 2013/0345294 | A1 * | 12/2013 | Yang | A61K 48/0083 |
| | | | | 435/320.1 |
| 2016/0326219 | A1 * | 11/2016 | Riedler | G01N 33/5088 |
| 2017/0298330 | A1 * | 10/2017 | Sato | C12N 9/22 |

FOREIGN PATENT DOCUMENTS

| | | |
|---|---|---|
| JP | 2015165776 A | 9/2015 |
| WO | 2004035628 A1 | 4/2004 |
| WO | 2011130540 | 10/2011 |
| WO | 2016167300 | 10/2016 |

OTHER PUBLICATIONS

Bacchus et al. Biomedically relevant circuit-design strategies in mammalian synthetic biology. Mol Systems Biol 9: 691, 2013.*
Bhattacharya et al. Impact of genetic variation on three dimensional structure and function of proteins. PLoS ONE 12(3): e0171355, 2017.*
Bork, P. Powers and pitfalls in sequence analysis: the 70% hurdle. Genome Res 10: 398-400, 2000.*
Bork, P. Go hunting in sequence databases but watch out for the traps. Trends in Genetics 12(10): 425-427, 1996.*
Brenner. S.E. Errors in genome annotation. Trends in Genetics 15:132-133, 1999.*
Doerks et al. Protein annotation: detective work for function prediction. Trends in Genetics 14:248-250, 1998.*
Endo et al. Strategies for development of optogenetic systems and their applications. J Photochem Photobiol C: Photochem Rev 30 : 10-23, published online Nov. 14, 2016.*
Fenton et al. Rheostat positions: a new classification of protein positions relevant to pharmacogenomics. Medicinal Chem Res 29: 1133-1146, 2020.*
Gierut et al. Strategies to achieve conditional gene mutation in mice. Cold Spring Harb Protoc. Apr. 1, 2014;2014(4):339-49. doi: 10.1101/pdb.top069807.*
Gross et al. Spying on cancer: molecular imaging in vivo with genetically encoded receptors. Cancer Cell 7: 5-15, 2005.*
Guo et al. Protein tolerance to random amino acid change. Proc Natl Acad Sci USA 101(25): 9205-9210, 2004.*
Hirrlinger et al. Split-Cre complementation indicates coincident activity of different genes in vivo. PLoS One 4(1): e4286, 2009.*
Hirrlinger et al. Split-CreERT2: Temporal control of DNA recombination mediated by Split-CRE protein fragment complementation. PLoS One 4(12): e8354, 2009.*
Kawano et al. Engineered pairs of distinct photoswitches for optogenetic control of cellular proteins. Nature Comm 6: 6256, 2015.*
Kawano et al. A photoactivatable Cre-loxP recombination system for optogenetic genome engineering. Nat Chem Biol 12: 1059-1064, 2016 (full article).*

(Continued)

*Primary Examiner* — Bridget E Bunner
(74) *Attorney, Agent, or Firm* — Suzannah K. Sundby, Esq.; Canady + Lortz LLP

(57) ABSTRACT

The purpose of the present invention is to provide a set of two polypeptides for use in light-dependent genetic recombination in which the N-terminal side fragment and the C-terminal side fragment of a Cre protein having an amino acid sequence of SEQ ID NO: 1 respectively bind to two proteins light-dependently forming a dimer.

16 Claims, 17 Drawing Sheets
Specification includes a Sequence Listing.

(56) References Cited

OTHER PUBLICATIONS

Kennedy et al. Rapid blue-light-mediated induction of protein interactions in living cells. Nature Methods 7(12): 973-975, 2010.*
Langer et al. A genetic screen identifies novel non-compatible loxP sites. Nucleic Acids Res 30(14): 3067-3077, 2002.*
Lee et al. Role of nucleotide sequences of loxP spacer region in Cre-mediated recombination. Gene 216: 55-65, 1998.*
Ngo et al. "Computational complexity, protein structure prediction, and the Levinthal paradox" in The Protein Folding Problem and Tertiary Structure Prediction, pp. 492-495, 1994.*
Nihongaki et al. Genetically engineered photoinducible homodimerization system with improved dimer-forming strategy. ACS Chem Biol 9: 617-621, 2014.*
Skolnick et al. From genes to protein structure and function: novel applications of computational approaches in the genomic era. Trends Biotechnol 18(1):34-39 2000.*
Smith et al. The challenges of genome sequence annotation or "the devil is in the details". Nature Biotechnol 15: 1222-1223, 1997.*
Taslimi et al. Optimized second-generation CRY2-CIB dimerizers and photoactivatable Cre recombinase. Nat Chem Biol 12: 425-430, online Apr. 2016.*
Thomson et al. Mutational analysis of LoxP sites for efficient Cre-mediated insertion into genomic DNA. Genesis 36: 162-167, 2003.*
Tokuriki et al. Stability effects of mutations and protein evolvability. Curr Opin Structural Biol 19: 596-604, 2009.*
Wang et al. Spatiotemporal control of gene expession by a light-switchable transgene system. Nature Methods 9(3): 266-269, 2012.*
Wells, J.A. Additivity of mutational effects in proteins. Biochemistry 29(37): 8509-8517, 1990.*
Wen et al. Split-Cre complementation restores activity on transgene excision in hair roots of transgene tobacco. PLoS One 9(10): e110290, 2014.*
Zhou et al. Investigating neuronal function with optically controllable proteins. Front Mol Neurosci 8: 37, 2015.*
Zoltowski et al. Conformational switching in the fungal light sensor Vivid. Science 316(5827): 1054-1057, 2007.*
Zoltowski et al. Light activation of the LOV protein Vivid generates a rapidly exchanging dimer. Biochem 47: 7012-7019, 2008.*
Zoltowski et al. Mechanism-based tuning of a LOV domain photoreceptor. Nature Chem Biol 5(11): 827-834, 2009.*
Guo et al. Structure or Cre recombinase complexed with DNA in a site-specific recombination synapse. Nature 389: 40-46, 1997.*
Kawano et al. Supplementary Information for A photoactivatable Cre-loxP recombinatio system for optogenetic genome engineering. Nature Chem Biol 12: 1059-1064, Oct. 2016; 68 total pages.*
Duplus-Bottin et al. A single-chain and fast-responding light-inducible Cre recombinase as a novel optogenetic switch. eLife 10: 61268, 2021 (27 total pages).*
Kawano et al. Supplementary Figure Information for Engineered pairs of distinct photoswitches for optogenetic control of cellular proteins. Nature Comm 6: 6256, 2015 (43 total pages).*
International Search Report received in PCT/JP2018/015136 mailed Jul. 10, 2018.
Written Opinion received in PCT/JP2018/015136 mailed Jul. 10, 2018.
Jullien et al., "Regulation of Cre recombinase by ligand-induced complementation of inactive fragments", Nov. 1, 2003, pp. e131, vol. 31, No. 21, Publisher: Nucleic Acids Res.
Kawano et al., "A photoactivatable CreloxP recombination system for optogenetic genome engineering", Oct. 10, 2016, pp. 1059-1064 (abstract provided), vol. 12, Publisher: Nature Chemical Biology.
Jullien et al., Conditional transgenesis using Dimerizable Cre (DiCre), Dec. 26, 2007, p. e1355, vol. 2, No. 12, Publisher: PLOS One.
Meinke et al., Cre Recombinase and Other Tyrosine Recombinases, Oct. 26, 2016, pp. 12785-12820, vol. 116, No. 20, Publisher: Chem Rev.
Mueller & Weber, Optogenetic tools for mammalian systems, Apr. 5, 2013, pp. 596-608, vol. 9, No. 4, Publisher: Mol Biosyst.
Nihongaki et al., Photoactivatable CRISPR-Cas9 for optogenetic genome editing, 2015, pp. 755-760, vol. 33, No. 7, Publisher: Nat Biotechnol.
Schindler et al., Photo-activatable Cre recombinase regulates gene expression in vivo, Sep. 9, 2015, p. 13627, vol. 5, Publisher: Sci Rep.
Toettcher et al., The promise of optogenetics in cell biology: interrogating molecular circuits in space and time, Jan. 1, 2011, pp. 35-8, vol. 8, No. 1, Publisher: Nat Methods.

* cited by examiner

Fig. 5

|  | Left arm | Spacer | Right arm |
|---|---|---|---|
| loxP: | ATAACTTCGTATAA | TGTATG | CTATACGAAGTTAT |
| lox2722: | ATAACTTCGTATAA | AGTATC | CTATACGAAGTTAT |
| lox66: | TACCGTTCGTATAA | TGTATG | CTATACGAAGTTAT |
| lox71: | ATAACTTCGTATAA | TGTATG | CTATACGAACGGTA |
| lox72: | TACCGTTCGTATAA | TGTATG | CTATACGAACGGTA |
| JTZ15: | ATAACTTCGTATAA | TGTATG | CTATACGAATAATT |
| JTZ17: | ATAAATTGCTATAA | TGTATG | CTATACGAAGTTAT |
| JTZ15-JTZ17: | ATAAATTGCTATAA | TGTATG | CTATACGAATAATT |

Fig. 14

MATSDEVRKNLMDMFRDRQAFSEHTWKMLLS
VCRSWAAWCKLNGTHTLYAPGGYDIMGYLDQI
GNRPNPQVELGPVDTSCALILCDLKQKDTPIVY
ASEAFLYMTGYSNAEVLGRNCRFLQSPDGMV
KPKSTRKYVDSNTINTMRKAIDRNAEVQVEVV
NFKKNGQRFVNFLTMIPVRDETGEYRYSMGF
QCETEGGSGGVPKKKRKVGSSGSGATNFSLLK
QAGDVEENPG

PLEVPKKKRKVGGHTLYAPGGYDIMGYLRQIR
NRPNPQVELGPVDTSCALILCDLKQKDTPIVYA
SEAFLYMTGYSNAEVLGRNCRFLQSPDGMVK
PKSTRKYVDSNTINTMRKAIDRNAEVQVEVVN
FKKNGQRFVNFLTMIPVRDETGEYRYSMGFQ
CETEGTNRKVWFPAEPEDVRDYLLYLQARGLAV
KTIQQHLGQLNMLHRRSGLPRPSDSNAVSLVM
RRIRKENVDAGERAKQALAFERTDFDQVRSLM
ENSDRCQDIRNLAFLGIAYNTLLRIAEIARIRVKD
ISRTDGGRMLIHIGRTKTLVSTAGVEKALSLGVT
KLVERWISVSGVADDPNNYLFCRVRKNGVAAP
SATSQLSTRALEGIFEATHRLIYGAKDDSGQRY
LAWSGHSARVGAARDMARAGVSIPEIMQAGG
WTNVNIVMNYIRNLDSETGAMVRLLEDGD

Fig. 15

MATSDEVRKNLMDMFRDRQAFSEHTWKMLLS
VCRSWAAWCKLNNRKWFPAEPEDVRDYLLYL
QARGLAVKTIQQHLGQLNMLHRRSGLGTHTLY
APGGYDIMGYLDQIGNRPNPQVELGPVDTSCA
LILCDLKQKDTPIVYASEAFLYMTGYSNAEVLG
RNCRFLQSPDGMVKPKSTRKYVDSNTINTMR
KAIDRNAEVQVEVVNFKKNGQRFVNFLTMIPV
RDETGEYRYSMGFQCETEGGSGGVPKKKRK
VGSGSGATNFSLLKQAGDVEENPG

PLEVPKKKRKVGGHTLYAPGGYDIMGYLRQIR
NRPNPQVELGPVDTSCALILCDLKQKDTPIVYA
SEAFLYMTGYSNAEVLGRNCRFLQSPDGMVK
PKSTRKYVDSNTINTMRKAIDRNAEVQVEVVN
FKKNGQRFVNFLTMIPVRDETGEYRYSMGFQ
CETEGTRPSDSNAVSLVMRRIRKENVDAGERA
KQALAFERTDFDQVRSLMENSDRCQDIRNLAF
LGIAYNTLLRIAEIARIRVKDISRTDGGRMLIHIG
RTKTLVSTAGVEKALSLGVTKLVERWISVSGVA
DDPNNYLFCRVRKNGVAAPSATSQLSTRALEG
IFEATHRLIYGAKDDSGQRYLAWSGHSARVGA
ARDMARAGVSIPEIMQAGGWTNVNVMNYIRN
LDSETGAMVRLLEDGD

Fig. 16

ATGGCCACCTCTGATGAAGTCAGGAAGAACCTGATGGACATGTTCAGGGACAGGCAGGCCTT
CTCTGAACACACCTGGAAGATGCTCCTGTCTGTGTGCAGATCCTGGGCTGCCTGGTGCAAGC
TGAACGGTACCCATACTCTTTATGCCCCCGGTGGATATGACATTATGGGATATCTGGACCAGAT
CGGCAACCGGCCAAACCCGCAGGTGGAACTGGGCCCCGTGGATACATCCTGCGCCTTGATTC
TTTGTGACCTGAAACAGAAAGACACCCCGATAGTTTACGCGAGTGAAGCCTTCCTCTACATGA
CAGGTTACAGCAACGCAGAGGTGCTGGGCCGGAATTGCCGGTTTCTGCAAAGCCCTGACGGC
ATGGTGAAGCCCAAGAGCACCCGGAAGTACGTGGATAGTAACACAATCAATACTATGCGCAA
GGCAATCGACAGGAATGCCGAGGTGCAGGTTGAAGTAGTCAATTTTAAAAAGAATGGACAGC
GATTTGTTAATTTCCTGACTATGATACCTGTTAGGGACGAAACAGGCGAGTATCGATACTCTAT
GGGATTCCAGTGCGAAACAGAAGGCGGAAGCGGTGGCGTGCCCAAGAAGAAGAGGAAAGT
CGGATCCGGCAGCGGCGCCACCAACTTCAGCCTGCTGAAGCAGGCCGGCGACGTGGAGGAG
AACCCCGGCCCCCTCGAGGTGCCCAAGAAGAAGAGGAAAGTCGGCGGACATACTCTTTATGC
CCCCGGTGGATATGACATTATGGGATATCTGAGGCAGATCAGGAACCGGCCAAACCCGCAGGT
GGAACTGGGCCCCGTGGATACATCCTGCGCCTTGATTCTTTGTGACCTGAAACAGAAAGACA
CCCCGATAGTTTACGCGAGTGAAGCCTTCCTCTACATGACAGGTTACAGCAACGCAGAGGTG
CTGGGCCGGAATTGCCGGTTTCTGCAAAGCCCTGACGGCATGGTGAAGCCCAAGAGCACCCG
GAAGTACGTGGATAGTAACACAATCAATACTATGCGCAAGGCAATCGACAGGAATGCCGAGG
TGCAGGTTGAAGTAGTCAATTTTAAAAAGAATGGACAGCGATTTGTTAATTTCCTGACTATGAT
ACCTGTTAGGGACGAAACAGGCGAGTATCGATACTCTATGGGATTCCAGTGCGAAACAGAAG
GTACCAACAGGAAATGGTTCCCTGCTGAACCTGAGGATGTGAGGGACTACCTCCTGTACCTG
CAAGCCAGAGGCCTGGCTGTGAAGACCATCCAACAGCACCTGGGCCAGCTCAACATGCTGC
ACAGGAGATCTGGCCTGCCTCGCCCTTCTGACTCCAATGCTGTGTCCCTGGTGATGAGGAGAA
TCAGAAAGGAGAATGTGGATGCTGGGGAGAGAGCCAAGCAGGCCCTGGCCTTTGAACGCAC
TGACTTTGACCAAGTCAGATCCCTGATGGAGAACTCTGACAGATGCCAGGACATCAGGAACC
TGGCCTTCCTGGGCATTGCCTACAACACCCTGCTGCGCATTGCCGAAATTGCCAGAATCAGAG
TGAAGGACATCTCCCGCACCGATGGTGGGAGAATGCTGATCCACATTGGCAGGACCAAGACC
CTGGTGTCCACAGCTGGTGTGGAGAAGGCCCTGTCCCTGGGGGTTACCAAGCTGGTGGAGAG
ATGGATCTCTGTGTCTGGTGTGGCTGATGACCCCAACAACTACCTGTTCTGCCGGGTCAGAAA
GAATGGTGTGGCTGCCCCTTCTGCCACCTCCCAACTGTCCACCCGGGCCCTGGAAGGGATCTT
TGAGGCCACCCACCGCCTGATCTATGGTGCCAAGGATGACTCTGGGCAGAGATACCTGGCCT
GGTCTGGCCACTCTGCCAGAGTGGGTGCTGCCAGGGACATGGCCAGGGCTGGTGTGTCCATC
CCTGAAATCATGCAGGCTGGTGGCTGGACCAATGTGAACATTGTGATGAACTACATCAGAAAC
CTGGACTCTGAGACTGGGGCCATGGTGAGGCTGCTCGAAGATGGGGAC

Fig. 17

ATGGCCACCTCTGATGAAGTCAGGAAGAACCTGATGGACATGTTCAGGGACAGGCAGGCCTT
CTCTGAACACACCTGGAAGATGCTCCTGTCTGTGTGCAGATCCTGGGCTGCCTGGTGCAAGC
TGAACAACAGGAAATGGTTCCCTGCTGAACCTGAGGATGTGAGGGACTACCTCCTGTACCTG
CAAGCCAGAGGCCTGGCTGTGAAGACCATCCAACAGCACCTGGGCCAGCTCAACATGCTGC
ACAGGAGATCTGGCCTGGGTACCCATACTCTTTATGCCCCCGGTGGATATGACATTATGGGATA
TCTGGACCAGATCGGCAACCGGCCAAACCCGCAGGTGGAACTGGGCCCCGTGGATACATCCT
GCGCCTTGATTCTTTGTGACCTGAAACAGAAAGACACCCCGATAGTTTACGCGAGTGAAGCC
TTCCTCTACATGACAGGTTACAGCAACGCAGAGGTGCTGGGCCCGGAATTGCCGGTTTCTGCA
AAGCCCTGACGGCATGGTGAAGCCCAAGAGCACCCGGAAGTACGTGGATAGTAACACAATCA
ATACTATGCGCAAGGCAATCGACAGGAATGCCGAGGTGCAGGTTGAAGTAGTCAATTTTAAA
AAGAATGGACAGCGATTTGTTAATTTCCTGACTATGATACCTGTTAGGGACGAAACAGGCGAG
TATCGATACTCTATGGGATTCCAGTGCGAAACAGAAGGCGGAAGCGGTGGCGTGCCCAAGAA
GAAGAGGAAAGTCGGATCCGGCAGCGGCGCCACCAACTTCAGCCTGCTGAAGCAGGCCGGC
GACGTGGAGGAGAACCCCGGCCCCCTCGAGGTGCCCAAGAAGAAGAGGAAAGTCGGCGGA
CATACTCTTTATGCCCCCGGTGGATATGACATTATGGGATATCTGAGGCAGATCAGGAACCGGC
CAAACCCGCAGGTGGAACTGGGCCCCGTGGATACATCCTGCGCCTTGATTCTTTGTGACCTGA
AACAGAAAGACACCCCGATAGTTTACGCGAGTGAAGCCTTCCTCTACATGACAGGTTACAGC
AACGCAGAGGTGCTGGGCCCGGAATTGCCGGTTTCTGCAAAGCCCTGACGGCATGGTGAAGCC
CAAGAGCACCCGGAAGTACGTGGATAGTAACACAATCAATACTATGCGCAAGGCAATCGACA
GGAATGCCGAGGTGCAGGTTGAAGTAGTCAATTTTAAAAAGAATGGACAGCGATTTGTTAATT
TCCTGACTATGATACCTGTTAGGGACGAAACAGGCGAGTATCGATACTCTATGGGATTCCAGTG
CGAAACAGAAGGTACCCGCCCTTCTGACTCCAATGCTGTGTCCCTGGTGATGAGGAGAATCA
GAAAGGAGAATGTGGATGCTGGGGAGAGAGCCAAGCAGGCCCTGGCCTTTGAACGCACTGA
CTTTGACCAAGTCAGATCCCTGATGGAGAACTCTGACAGATGCCAGGACATCAGGAACCTGG
CCTTCCTGGGCATTGCCTACAACACCCTGCTGCGCATTGCCGAAATTGCCAGAATCAGAGTGA
AGGACATCTCCCGCACCGATGGTGGGAGAATGCTGATCCACATTGGCAGGACCAAGACCCTG
GTGTCCACAGCTGGTGTGGAGAAGGCCCTGTCCCTGGGGGTTACCAAGCTGGTGGAGAGATG
GATCTCTGTGTCTGGTGTGGCTGATGACCCCAACAACTACCTGTTCTGCCGGGTCAGAAAGAA
TGGTGTGGCTGCCCCTTCTGCCACCTCCAACTGTCCACCCGGGCCCTGGAAGGGATCTTTGA
GGCCACCCACCGCCTGATCTATGGTGCCAAGGATGACTCTGGGCAGAGATACCTGGCCTGGTC
TGGCCACTCTGCCAGAGTGGGTGCTGCCAGGGACATGGCCAGGGCTGGTGTGTCCATCCCTG
AAATCATGCAGGCTGGTGGCTGGACCAATGTGAACATTGTGATGAACTACATCAGAAACCTG
GACTCTGAGACTGGGGCCATGGTGAGGCTGCTCGAAGATGGGGAC

```
                        SEQUENCE LISTING

<160> NUMBER OF SEQ ID NOS: 31

<210> SEQ ID NO 1
<211> LENGTH: 343
<212> TYPE: PRT
<213> ORGANISM: Bacteriophage P1

<400> SEQUENCE: 1

Met Ser Asn Leu Leu Thr Val His Gln Asn Leu Pro Ala Leu Pro Val
1               5                   10                  15

Asp Ala Thr Ser Asp Glu Val Arg Lys Asn Leu Met Asp Met Phe Arg
            20                  25                  30

Asp Arg Gln Ala Phe Ser Glu His Thr Trp Lys Met Leu Leu Ser Val
        35                  40                  45

Cys Arg Ser Trp Ala Ala Trp Cys Lys Leu Asn Asn Arg Lys Trp Phe
    50                  55                  60

Pro Ala Glu Pro Glu Asp Val Arg Asp Tyr Leu Leu Tyr Leu Gln Ala
65                  70                  75                  80

Arg Gly Leu Ala Val Lys Thr Ile Gln Gln His Leu Gly Gln Leu Asn
                85                  90                  95

Met Leu His Arg Arg Ser Gly Leu Pro Arg Pro Ser Asp Ser Asn Ala
            100                 105                 110

Val Ser Leu Val Met Arg Arg Ile Arg Lys Glu Asn Val Asp Ala Gly
```

```
            115                 120                 125
Glu Arg Ala Lys Gln Ala Leu Ala Phe Glu Arg Thr Asp Phe Asp Gln
    130                 135                 140

Val Arg Ser Leu Met Glu Asn Ser Asp Arg Cys Gln Asp Ile Arg Asn
145                 150                 155                 160

Leu Ala Phe Leu Gly Ile Ala Tyr Asn Thr Leu Leu Arg Ile Ala Glu
                165                 170                 175

Ile Ala Arg Ile Arg Val Lys Asp Ile Ser Arg Thr Asp Gly Gly Arg
            180                 185                 190

Met Leu Ile His Ile Gly Arg Thr Lys Thr Leu Val Ser Thr Ala Gly
        195                 200                 205

Val Glu Lys Ala Leu Ser Leu Gly Val Thr Lys Leu Val Glu Arg Trp
    210                 215                 220

Ile Ser Val Ser Gly Val Ala Asp Asp Pro Asn Asn Tyr Leu Phe Cys
225                 230                 235                 240

Arg Val Arg Lys Asn Gly Val Ala Ala Pro Ser Ala Thr Ser Gln Leu
                245                 250                 255

Ser Thr Arg Ala Leu Glu Gly Ile Phe Glu Ala Thr His Arg Leu Ile
            260                 265                 270

Tyr Gly Ala Lys Asp Asp Ser Gly Gln Arg Tyr Leu Ala Trp Ser Gly
        275                 280                 285

His Ser Ala Arg Val Gly Ala Ala Arg Asp Met Ala Arg Ala Gly Val
    290                 295                 300

Ser Ile Pro Glu Ile Met Gln Ala Gly Gly Trp Thr Asn Val Asn Ile
305                 310                 315                 320

Val Met Asn Tyr Ile Arg Asn Leu Asp Ser Glu Thr Gly Ala Met Val
                325                 330                 335

Arg Leu Leu Glu Asp Gly Asp
            340

<210> SEQ ID NO 2
<211> LENGTH: 186
<212> TYPE: PRT
<213> ORGANISM: Neurospora crassa

<400> SEQUENCE: 2

Met Ser His Thr Val Asn Ser Ser Thr Met Asn Pro Trp Glu Val Glu
1               5                   10                  15

Ala Tyr Gln Gln Tyr His Tyr Asp Pro Arg Thr Ala Pro Thr Ala Asn
                20                  25                  30

Pro Leu Phe Phe His Thr Leu Tyr Ala Pro Gly Gly Tyr Asp Ile Met
            35                  40                  45

Gly Tyr Leu Ile Gln Ile Met Asn Arg Pro Asn Pro Gln Val Glu Leu
        50                  55                  60

Gly Pro Val Asp Thr Ser Cys Ala Leu Ile Leu Cys Asp Leu Lys Gln
65                  70                  75                  80

Lys Asp Thr Pro Ile Val Tyr Ala Ser Glu Ala Phe Leu Tyr Met Thr
                85                  90                  95

Gly Tyr Ser Asn Ala Glu Val Leu Gly Arg Asn Cys Arg Phe Leu Gln
            100                 105                 110

Ser Pro Asp Gly Met Val Lys Pro Lys Ser Thr Arg Lys Tyr Val Asp
        115                 120                 125

Ser Asn Thr Ile Asn Thr Met Arg Lys Ala Ile Asp Arg Asn Ala Glu
    130                 135                 140
```

```
Val Gln Val Glu Val Val Asn Phe Lys Lys Asn Gly Gln Arg Phe Val
145                 150                 155                 160

Asn Phe Leu Thr Met Ile Pro Val Arg Asp Glu Thr Gly Glu Tyr Arg
                165                 170                 175

Tyr Ser Met Gly Phe Gln Cys Glu Thr Glu
            180                 185

<210> SEQ ID NO 3
<211> LENGTH: 16
<212> TYPE: PRT
<213> ORGANISM: Artificial Sequence
<220> FEATURE:
<223> OTHER INFORMATION: 16 a.a. linker

<400> SEQUENCE: 3

Leu Glu Ala Ser Pro Ser Asn Pro Gly Ala Ser Asn Gly Ser Gly Thr
1               5                   10                  15

<210> SEQ ID NO 4
<211> LENGTH: 10
<212> TYPE: PRT
<213> ORGANISM: Artificial Sequence
<220> FEATURE:
<223> OTHER INFORMATION: 10 a.a. linker

<400> SEQUENCE: 4

Leu Glu Ala Ser Thr Gly Gly Ser Gly Thr
1               5                   10

<210> SEQ ID NO 5

<400> SEQUENCE: 5

000

<210> SEQ ID NO 6
<211> LENGTH: 22
<212> TYPE: PRT
<213> ORGANISM: porcine teschovirus-1

<400> SEQUENCE: 6

Gly Ser Gly Ala Thr Asn Phe Ser Leu Leu Lys Gln Ala Gly Asp Val
1               5                   10                  15

Glu Glu Asn Pro Gly Pro
            20

<210> SEQ ID NO 7
<211> LENGTH: 34
<212> TYPE: DNA
<213> ORGANISM: Bacteriophage P1

<400> SEQUENCE: 7
ataacttcgt ataatgtatg ctatacgaag ttat                              34

<210> SEQ ID NO 8
<211> LENGTH: 34
<212> TYPE: DNA
<213> ORGANISM: Artificial Sequence
<220> FEATURE:
<223> OTHER INFORMATION: lox2722

<400> SEQUENCE: 8
ataacttcgt ataaagtatc ctatacgaag ttat                              34
```

```
<210> SEQ ID NO 9
<211> LENGTH: 34
<212> TYPE: DNA
<213> ORGANISM: Artificial Sequence
<220> FEATURE:
<223> OTHER INFORMATION: lox66

<400> SEQUENCE: 9
taccgttcgt ataatgtatg ctatacgaag ttat                               34

<210> SEQ ID NO 10
<211> LENGTH: 34
<212> TYPE: DNA
<213> ORGANISM: Artificial Sequence
<220> FEATURE:
<223> OTHER INFORMATION: lox71

<400> SEQUENCE: 10
ataacttcgt ataatgtatg ctatacgaac ggta                               34

<210> SEQ ID NO 11
<211> LENGTH: 34
<212> TYPE: DNA
<213> ORGANISM: Artificial Sequence
<220> FEATURE:
<223> OTHER INFORMATION: JT15

<400> SEQUENCE: 11
ataacttcgt ataatgtatg ctatacgaat aatt                               34

<210> SEQ ID NO 12
<211> LENGTH: 34
<212> TYPE: DNA
<213> ORGANISM: Artificial Sequence
<220> FEATURE:
<223> OTHER INFORMATION: JTZ17

<400> SEQUENCE: 12
ataaattgct ataatgtatg ctatacgaag ttat                               34

<210> SEQ ID NO 13
<211> LENGTH: 34
<212> TYPE: DNA
<213> ORGANISM: Artificial Sequence
<220> FEATURE:
<223> OTHER INFORMATION: lox72

<400> SEQUENCE: 13
taccgttcgt ataatgtatg ctatacgaac ggta                               34

<210> SEQ ID NO 14
<211> LENGTH: 34
<212> TYPE: DNA
<213> ORGANISM: Artificial Sequence
<220> FEATURE:
<223> OTHER INFORMATION: JA15-JTZ17

<400> SEQUENCE: 14
ataaattgct ataatgtatg ctatacgaat aatt                               34

<210> SEQ ID NO 15
<211> LENGTH: 150
<212> TYPE: PRT
<213> ORGANISM: Artificial Sequence
<220> FEATURE:
<223> OTHER INFORMATION: pMag
```

```
<400> SEQUENCE: 15

His Thr Leu Tyr Ala Pro Gly Gly Tyr Asp Ile Met Gly Tyr Leu Arg
1               5                   10                  15

Gln Ile Arg Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
            115                 120                 125

Met Ile Pro Val Arg Asp Glu Thr Gly Glu Tyr Arg Tyr Ser Met Gly
130                 135                 140

Phe Gln Cys Glu Thr Glu
145                 150

<210> SEQ ID NO 16
<211> LENGTH: 150
<212> TYPE: PRT
<213> ORGANISM: Artificial Sequence
<220> FEATURE:
<223> OTHER INFORMATION: pMagHigh1

<400> SEQUENCE: 16

His Thr Leu Tyr Ala Pro Gly Gly Tyr Asp Ile Met Gly Tyr Leu Arg
1               5                   10                  15

Gln Ile Arg Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Ile Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
            115                 120                 125

Ile Ile Pro Val Arg Asp Glu Thr Gly Glu Tyr Arg Tyr Ser Met Gly
130                 135                 140

Phe Gln Cys Glu Thr Glu
145                 150

<210> SEQ ID NO 17
<211> LENGTH: 150
<212> TYPE: PRT
<213> ORGANISM: Artificial Sequence
<220> FEATURE:
<223> OTHER INFORMATION: pMagFast1
```

<400> SEQUENCE: 17

```
His Thr Leu Tyr Ala Pro Gly Gly Tyr Asp Ile Met Gly Tyr Leu Arg
1               5                   10                  15

Gln Ile Arg Asn Arg Pro Asn Pro Gln Val Glu Leu Gly Pro Val Asp
                20                  25                  30

Thr Ser Cys Ala Leu Ile Leu Cys Asp Leu Lys Gln Lys Asp Thr Pro
            35                  40                  45

Val Val Tyr Ala Ser Glu Ala Phe Leu Tyr Met Thr Gly Tyr Ser Asn
        50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
                100                 105                 110

Val Val Asn Phe Lys Lys Asn Gly Gln Arg Phe Val Asn Phe Leu Thr
            115                 120                 125

Met Ile Pro Val Arg Asp Glu Thr Gly Glu Tyr Arg Tyr Ser Met Gly
130                 135                 140

Phe Gln Cys Glu Thr Glu
145                 150
```

<210> SEQ ID NO 18
<211> LENGTH: 150
<212> TYPE: PRT
<213> ORGANISM: Artificial Sequence
<220> FEATURE:
<223> OTHER INFORMATION: pMagFast2

<400> SEQUENCE: 18

```
His Thr Leu Tyr Ala Pro Gly Gly Tyr Asp Ile Met Gly Tyr Leu Arg
1               5                   10                  15

Gln Ile Arg Asn Arg Pro Asn Pro Gln Val Glu Leu Gly Pro Val Asp
                20                  25                  30

Thr Ser Cys Ala Leu Val Leu Cys Asp Leu Lys Gln Lys Asp Thr Pro
            35                  40                  45

Val Val Tyr Ala Ser Glu Ala Phe Leu Tyr Met Thr Gly Tyr Ser Asn
        50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
                100                 105                 110

Val Val Asn Phe Lys Lys Asn Gly Gln Arg Phe Val Asn Phe Leu Thr
            115                 120                 125

Met Ile Pro Val Arg Asp Glu Thr Gly Glu Tyr Arg Tyr Ser Met Gly
130                 135                 140

Phe Gln Cys Glu Thr Glu
145                 150
```

<210> SEQ ID NO 19
<211> LENGTH: 150
<212> TYPE: PRT
<213> ORGANISM: Artificial Sequence
<220> FEATURE:

<223> OTHER INFORMATION: nMag

<400> SEQUENCE: 19

His Thr Leu Tyr Ala Pro Gly Gly Tyr Asp Ile Met Gly Tyr Leu Asp
1               5                   10                  15

Gln Ile Gly Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150

<210> SEQ ID NO 20
<211> LENGTH: 150
<212> TYPE: PRT
<213> ORGANISM: Artificial Sequence
<220> FEATURE:
<223> OTHER INFORMATION: nMagHigh1

<400> SEQUENCE: 20

His Thr Leu Tyr Ala Pro Gly Gly Tyr Asp Ile Met Gly Tyr Leu Asp
1               5                   10                  15

Gln Ile Gly Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Ile Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Ile Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Ile Ile Pro Val Arg Asp Glu Thr Gly Glu Tyr Arg Tyr Ser Met Gly
    130                 135                 140

Phe Gln Cys Glu Thr Glu
145                 150

<210> SEQ ID NO 21
<211> LENGTH: 150
<212> TYPE: PRT
<213> ORGANISM: Artificial Sequence
<220> FEATURE:
<223> OTHER INFORMATION: nMagFast1

<400> SEQUENCE: 21

His Thr Leu Tyr Ala Pro Gly Gly Tyr Asp Ile Met Gly Tyr Leu Asp
1               5                   10                  15

Gln Ile Gly Asn Arg Pro Asn Pro Gln Val Glu Leu Gly Pro Val Asp
            20                  25                  30

Thr Ser Cys Ala Leu Ile Leu Cys Asp Leu Lys Gln Lys Asp Thr Pro
        35                  40                  45

Val Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150

<210> SEQ ID NO 22
<211> LENGTH: 150
<212> TYPE: PRT
<213> ORGANISM: Artificial Sequence
<220> FEATURE:
<223> OTHER INFORMATION: nMagFast2

<400> SEQUENCE: 22

His Thr Leu Tyr Ala Pro Gly Gly Tyr Asp Ile Met Gly Tyr Leu Asp
1               5                   10                  15

Gln Ile Gly Asn Arg Pro Asn Pro Gln Val Glu Leu Gly Pro Val Asp
            20                  25                  30

Thr Ser Cys Ala Leu Val Leu Cys Asp Leu Lys Gln Lys Asp Thr Pro
        35                  40                  45

Val Val Tyr Ala Ser Glu Ala Phe Leu Tyr Met Thr Gly Tyr Ser Asn
    50                  55                  60

Ala Glu Val Leu Gly Arg Asn Cys Arg Phe Leu Gln Ser Pro Asp Gly
65                  70                  75                  80

Met Val Lys Pro Lys Ser Thr Arg Lys Tyr Val Asp Ser Asn Thr Ile
                85                  90                  95

Asn Thr Met Arg Lys Ala Ile Asp Arg Asn Ala Glu Val Gln Val Glu
            100                 105                 110

Val Val Asn Phe Lys Lys Asn Gly Gln Arg Phe Val Asn Phe Leu Thr
        115                 120                 125

Met Ile Pro Val Arg Asp Glu Thr Gly Glu Tyr Arg Tyr Ser Met Gly
    130                 135                 140

Phe Gln Cys Glu Thr Glu
145                 150

<210> SEQ ID NO 23
<211> LENGTH: 8
<212> TYPE: PRT

<213> ORGANISM: Homo sapiens

<400> SEQUENCE: 23

Val Pro Lys Lys Lys Arg Lys Val
1               5

<210> SEQ ID NO 24
<211> LENGTH: 21
<212> TYPE: PRT
<213> ORGANISM: Homo sapiens

<400> SEQUENCE: 24

Lys Arg Thr Ala Asp Gly Ser Glu Phe Glu Ser Pro Lys Lys Arg
1               5                   10                  15

Lys Val Glu Ala Ser
            20

<210> SEQ ID NO 25
<211> LENGTH: 231
<212> TYPE: PRT
<213> ORGANISM: Artificial Sequence
<220> FEATURE:
<223> OTHER INFORMATION: polypeptide of PA-Cre having CreN59

<400> SEQUENCE: 25

Met Ala Thr Ser Asp Glu Val Arg Lys Asn Leu Met Asp Met Phe Arg
1               5                   10                  15

Asp Arg Gln Ala Phe Ser Glu His Thr Trp Lys Met Leu Leu Ser Val
                20                  25                  30

Cys Arg Ser Trp Ala Ala Trp Cys Lys Leu Asn Gly His Thr Leu
            35                  40                  45

Tyr Ala Pro Gly Gly Tyr Asp Ile Met Gly Tyr Leu Asp Gln Ile Gly
        50                  55                  60

Asn Arg Pro Asn Pro Gln Val Glu Leu Gly Pro Val Asp Thr Ser Cys
65                  70                  75                  80

Ala Leu Ile Leu Cys Asp Leu Lys Gln Lys Asp Thr Pro Ile Val Tyr
                85                  90                  95

Ala Ser Glu Ala Phe Leu Tyr Met Thr Gly Tyr Ser Asn Ala Glu Val
            100                 105                 110

Leu Gly Arg Asn Cys Arg Phe Leu Gln Ser Pro Asp Gly Met Val Lys
        115                 120                 125

Pro Lys Ser Thr Arg Lys Tyr Val Asp Ser Asn Thr Ile Asn Thr Met
130                 135                 140

Arg Lys Ala Ile Asp Arg Asn Ala Glu Val Gln Val Glu Val Val Asn
145                 150                 155                 160

Phe Lys Lys Asn Gly Gln Arg Phe Val Asn Phe Leu Thr Met Ile Pro
                165                 170                 175

Val Arg Asp Glu Thr Gly Glu Tyr Arg Tyr Ser Met Gly Phe Gln Cys
            180                 185                 190

Glu Thr Glu Gly Gly Ser Gly Gly Val Pro Lys Lys Arg Lys Val
        195                 200                 205

Gly Ser Gly Ser Gly Ala Thr Asn Phe Ser Leu Leu Lys Gln Ala Gly
        210                 215                 220

Asp Val Glu Glu Asn Pro Gly
225                 230

<210> SEQ ID NO 26
<211> LENGTH: 449

<212> TYPE: PRT
<213> ORGANISM: Artificial Sequence
<220> FEATURE:
<223> OTHER INFORMATION: polypeptide of PA-Cre having CreC60

<400> SEQUENCE: 26

```
Pro Leu Glu Val Pro Lys Lys Arg Lys Val Gly Gly His Thr Leu
1               5                   10                  15

Tyr Ala Pro Gly Gly Tyr Asp Ile Met Gly Tyr Leu Arg Gln Ile Arg
            20                  25                  30

Asn Arg Pro Asn Pro Gln Val Glu Leu Gly Pro Val Asp Thr Ser Cys
                35                  40                  45

Ala Leu Ile Leu Cys Asp Leu Lys Gln Lys Asp Thr Pro Ile Val Tyr
        50                  55                  60

Ala Ser Glu Ala Phe Leu Tyr Met Thr Gly Tyr Ser Asn Ala Glu Val
65                  70                  75                  80

Leu Gly Arg Asn Cys Arg Phe Leu Gln Ser Pro Asp Gly Met Val Lys
                85                  90                  95

Pro Lys Ser Thr Arg Lys Tyr Val Asp Ser Asn Thr Ile Asn Thr Met
            100                 105                 110

Arg Lys Ala Ile Asp Arg Asn Ala Glu Val Gln Val Glu Val Val Asn
        115                 120                 125

Phe Lys Lys Asn Gly Gln Arg Phe Val Asn Phe Leu Thr Met Ile Pro
130                 135                 140

Val Arg Asp Glu Thr Gly Glu Tyr Arg Tyr Ser Met Gly Phe Gln Cys
145                 150                 155                 160

Glu Thr Glu Gly Thr Asn Arg Lys Trp Phe Pro Ala Glu Pro Glu Asp
                165                 170                 175

Val Arg Asp Tyr Leu Leu Tyr Leu Gln Ala Arg Gly Leu Ala Val Lys
            180                 185                 190

Thr Ile Gln Gln His Leu Gly Gln Leu Asn Met Leu His Arg Arg Ser
        195                 200                 205

Gly Leu Pro Arg Pro Ser Asp Ser Asn Ala Val Ser Leu Val Met Arg
210                 215                 220

Arg Ile Arg Lys Glu Asn Val Asp Ala Gly Glu Arg Ala Lys Gln Ala
225                 230                 235                 240

Leu Ala Phe Glu Arg Thr Asp Phe Asp Gln Val Arg Ser Leu Met Glu
                245                 250                 255

Asn Ser Asp Arg Cys Gln Asp Ile Arg Asn Leu Ala Phe Leu Gly Ile
            260                 265                 270

Ala Tyr Asn Thr Leu Leu Arg Ile Ala Glu Ile Ala Arg Ile Arg Val
        275                 280                 285

Lys Asp Ile Ser Arg Thr Asp Gly Gly Arg Met Leu Ile His Ile Gly
290                 295                 300

Arg Thr Lys Thr Leu Val Ser Thr Ala Gly Val Glu Lys Ala Leu Ser
305                 310                 315                 320

Leu Gly Val Thr Lys Leu Val Glu Arg Trp Ile Ser Val Ser Gly Val
                325                 330                 335

Ala Asp Asp Pro Asn Asn Tyr Leu Phe Cys Arg Val Arg Lys Asn Gly
            340                 345                 350

Val Ala Ala Pro Ser Ala Thr Ser Gln Leu Ser Thr Arg Ala Leu Glu
        355                 360                 365

Gly Ile Phe Glu Ala Thr His Arg Leu Ile Tyr Gly Ala Lys Asp Asp
370                 375                 380
```

```
Ser Gly Gln Arg Tyr Leu Ala Trp Ser Gly His Ser Ala Arg Val Gly
385                 390                 395                 400

Ala Ala Arg Asp Met Ala Arg Ala Gly Val Ser Ile Pro Glu Ile Met
            405                 410                 415

Gln Ala Gly Gly Trp Thr Asn Val Asn Ile Val Met Asn Tyr Ile Arg
        420                 425                 430

Asn Leu Asp Ser Glu Thr Gly Ala Met Val Arg Leu Leu Glu Asp Gly
    435                 440                 445

Asp

<210> SEQ ID NO 27
<211> LENGTH: 276
<212> TYPE: PRT
<213> ORGANISM: Artificial Sequence
<220> FEATURE:
<223> OTHER INFORMATION: polypeptide of PA-Cre having CreN104

<400> SEQUENCE: 27

Met Ala Thr Ser Asp Glu Val Arg Lys Asn Leu Met Asp Met Phe Arg
1               5                   10                  15

Asp Arg Gln Ala Phe Ser Glu His Thr Trp Lys Met Leu Leu Ser Val
            20                  25                  30

Cys Arg Ser Trp Ala Ala Trp Cys Lys Leu Asn Asn Arg Lys Trp Phe
        35                  40                  45

Pro Ala Glu Pro Glu Asp Val Arg Asp Tyr Leu Leu Tyr Leu Gln Ala
    50                  55                  60

Arg Gly Leu Ala Val Lys Thr Ile Gln Gln His Leu Gly Gln Leu Asn
65                  70                  75                  80

Met Leu His Arg Arg Ser Gly Leu Gly Thr His Thr Leu Tyr Ala Pro
                85                  90                  95

Gly Gly Tyr Asp Ile Met Gly Tyr Leu Asp Gln Ile Gly Asn Arg Pro
            100                 105                 110

Asn Pro Gln Val Glu Leu Gly Pro Val Asp Thr Ser Cys Ala Leu Ile
        115                 120                 125

Leu Cys Asp Leu Lys Gln Lys Asp Thr Pro Ile Val Tyr Ala Ser Glu
130                 135                 140

Ala Phe Leu Tyr Met Thr Gly Tyr Ser Asn Ala Glu Val Leu Gly Arg
145                 150                 155                 160

Asn Cys Arg Phe Leu Gln Ser Pro Asp Gly Met Val Lys Pro Lys Ser
                165                 170                 175

Thr Arg Lys Tyr Val Asp Ser Asn Thr Ile Asn Thr Met Arg Lys Ala
            180                 185                 190

Ile Asp Arg Asn Ala Glu Val Gln Val Glu Val Asn Phe Lys Lys
        195                 200                 205

Asn Gly Gln Arg Phe Val Asn Phe Leu Thr Met Ile Pro Val Arg Asp
210                 215                 220

Glu Thr Gly Glu Tyr Arg Tyr Ser Met Gly Phe Gln Cys Glu Thr Glu
225                 230                 235                 240

Gly Gly Ser Gly Gly Val Pro Lys Lys Arg Lys Val Gly Ser Gly
                245                 250                 255

Ser Gly Ala Thr Asn Phe Ser Leu Leu Lys Gln Ala Gly Asp Val Glu
            260                 265                 270

Glu Asn Pro Gly
        275
```

<210> SEQ ID NO 28
<211> LENGTH: 403
<212> TYPE: PRT
<213> ORGANISM: Artificial Sequence
<220> FEATURE:
<223> OTHER INFORMATION: polypeptide of PA-Cre having CreC106

<400> SEQUENCE: 28

```
Pro Leu Glu Val Pro Lys Lys Arg Lys Val Gly Gly His Thr Leu
1               5                   10                  15

Tyr Ala Pro Gly Gly Tyr Asp Ile Met Gly Tyr Leu Arg Gln Ile Arg
                20                  25                  30

Asn Arg Pro Asn Pro Gln Val Glu Leu Gly Pro Val Asp Thr Ser Cys
        35                  40                  45

Ala Leu Ile Leu Cys Asp Leu Lys Gln Lys Asp Thr Pro Ile Val Tyr
    50                  55                  60

Ala Ser Glu Ala Phe Leu Tyr Met Thr Gly Tyr Ser Asn Ala Glu Val
65                  70                  75                  80

Leu Gly Arg Asn Cys Arg Phe Leu Gln Ser Pro Asp Gly Met Val Lys
                85                  90                  95

Pro Lys Ser Thr Arg Lys Tyr Val Asp Ser Asn Thr Ile Asn Thr Met
            100                 105                 110

Arg Lys Ala Ile Asp Arg Asn Ala Glu Val Gln Val Glu Val Val Asn
        115                 120                 125

Phe Lys Lys Asn Gly Gln Arg Phe Val Asn Phe Leu Thr Met Ile Pro
    130                 135                 140

Val Arg Asp Glu Thr Gly Glu Tyr Arg Tyr Ser Met Gly Phe Gln Cys
145                 150                 155                 160

Glu Thr Glu Gly Thr Arg Pro Ser Asp Ser Asn Ala Val Ser Leu Val
                165                 170                 175

Met Arg Arg Ile Arg Lys Glu Asn Val Asp Ala Gly Glu Arg Ala Lys
            180                 185                 190

Gln Ala Leu Ala Phe Glu Arg Thr Asp Phe Asp Gln Val Arg Ser Leu
        195                 200                 205

Met Glu Asn Ser Asp Arg Cys Gln Asp Ile Arg Asn Leu Ala Phe Leu
    210                 215                 220

Gly Ile Ala Tyr Asn Thr Leu Leu Arg Ile Ala Glu Ile Ala Arg Ile
225                 230                 235                 240

Arg Val Lys Asp Ile Ser Arg Thr Asp Gly Gly Arg Met Leu Ile His
                245                 250                 255

Ile Gly Arg Thr Lys Thr Leu Val Ser Thr Ala Gly Val Glu Lys Ala
            260                 265                 270

Leu Ser Leu Gly Val Thr Lys Leu Val Glu Arg Trp Ile Ser Val Ser
        275                 280                 285

Gly Val Ala Asp Asp Pro Asn Asn Tyr Leu Phe Cys Arg Val Arg Lys
    290                 295                 300

Asn Gly Val Ala Ala Pro Ser Ala Thr Ser Gln Leu Ser Thr Arg Ala
305                 310                 315                 320

Leu Glu Gly Ile Phe Glu Ala Thr His Arg Leu Ile Tyr Gly Ala Lys
                325                 330                 335

Asp Asp Ser Gly Gln Arg Tyr Leu Ala Trp Ser Gly His Ser Ala Arg
            340                 345                 350

Val Gly Ala Ala Arg Asp Met Ala Arg Ala Gly Val Ser Ile Pro Glu
        355                 360                 365

Ile Met Gln Ala Gly Gly Trp Thr Asn Val Asn Ile Val Met Asn Tyr
```

```
                370             375             380
Ile Arg Asn Leu Asp Ser Glu Thr Gly Ala Met Val Arg Leu Leu Glu
385             390             395             400

Asp Gly Asp

<210> SEQ ID NO 29
<211> LENGTH: 2040
<212> TYPE: DNA
<213> ORGANISM: Artificial Sequence
<220> FEATURE:
<223> OTHER INFORMATION: PA-Cre having CreN59 and CreC60

<400> SEQUENCE: 29
atggccacct ctgatgaagt caggaagaac ctgatggaca tgttcaggga caggcaggcc    60
ttctctgaac acacctggaa gatgctcctg tctgtgtgca gatcctgggc tgcctggtgc   120
aagctgaacg gtacccatac tctttatgcc cccggtggat atgacattat gggatatctg   180
gaccagatcg gcaaccggcc aaacccgcag gtggaactgg ccccgtggat acatcctgc    240
gccttgattc tttgtgacct gaaacagaaa gacaccccga tagtttacgc gagtgaagcc   300
ttcctctaca tgacaggtta cagcaacgca gaggtgctgg ccggaattgc cggtttctg    360
caaagccctg acggcatggt gaagcccaag agcacccgga gtacgtgga tagtaacaca    420
atcaatacta tgcgcaaggc aatcgacagg aatgccgagg tgcaggttga agtagtcaat    480
tttaaaaaga tggacagcga ttttgttaat ttcctgacta tgatacctgt tagggacgaa    540
acaggcgagt atcgatactc tatgggattc cagtgcgaaa cagaaggcgg aagcggtggc    600
gtgcccaaga agaagaggaa agtcggatcc ggcagcggcg ccaccaactt cagcctgctg    660
aagcaggccg cgacgtgga ggagaaccc ggccccctcg aggtgcccaa gaagaagagg     720
aaagtcggcg gacatactct ttatgcccc ggtggatatg acattatggg atatctgagg    780
cagatcagga accggccaaa cccgcaggtg gaactgggcc cgtggatac atcctgcgcc    840
ttgattcttt gtgacctgaa acagaaagac accccgatag tttacgcgag tgaagccttc    900
ctctacatga caggttacag caacgcagag gtgctgggcc ggaattgccg gtttctgcaa    960
agccctgacg gcatggtgaa gcccaagagc acccggaagt acgtggatag taacacaatc   1020
aatactatgc gcaaggcaat cgacaggaat gccgaggtgc aggttgaagt agtcaatttt   1080
aaaaagaatg acagcgatt tgttaatttc ctgactatga tacctgttag ggacgaaaca   1140
ggcgagtatc gatactctat gggattccag tgcgaaacag aaggtaccaa caggaaatgg   1200
ttccctgcta acctgagga tgtgaggac tacctcctgt acctgcaagc cagaggcctg    1260
gctgtgaaga ccatccaaca gcacctgggc cagctcaaca tgctgcacag gagatctggc   1320
ctgcctcgcc cttctgactc caatgctgtg tccctggtga tgaggagaat cagaaaggag   1380
aatgtggatg ctggggagag agccaagcag gccctggcct ttgaacgcac tgactttgac   1440
caagtcagat ccctgatgga gaactctgac agatgccagg acatcaggaa cctggccttc   1500
ctgggcattg cctacaacac cctgctgcgc attgccgaaa ttgccagaat cagagtgaag   1560
gacatctccc gcaccgatgg tgggagaatg ctgatccaca ttggcaggac caagaccctg   1620
gtgtccacag ctggtgtgga aaggccctg tccctggggg ttaccaagct ggtggagaga   1680
tggatctctg tgtctggtgt ggctgatgac cccaacaact acctgttctg ccgggtcaga   1740
aagaatggtg tggctgcccc ttctgccacc tcccaactgt ccaccggggc cctggaaggg   1800
atctttgagg ccacccaccg cctgatctat ggtgccaagg atgactctgg gcagagatac   1860
```

| | |
|---|---|
| ctggcctggt ctggccactc tgccagagtg ggtgctgcca gggacatggc cagggctggt | 1920 |
| gtgtccatcc ctgaaatcat gcaggctggt ggctggacca atgtgaacat tgtgatgaac | 1980 |
| tacatcagaa acctggactc tgagactggg gccatggtga ggctgctcga agatggggac | 2040 |

<210> SEQ ID NO 30
<211> LENGTH: 2037
<212> TYPE: DNA
<213> ORGANISM: Artificial Sequence
<220> FEATURE:
<223> OTHER INFORMATION: PA-Cre having CreN104 and CreC106

<400> SEQUENCE: 30

| | |
|---|---|
| atggccacct ctgatgaagt caggaagaac ctgatggaca tgttcaggga caggcaggcc | 60 |
| ttctctgaac acacctggaa gatgctcctg tctgtgtgca gatcctgggc tgcctggtgc | 120 |
| aagctgaaca acaggaaatg gttccctgct gaacctgagg atgtgaggga ctacctcctg | 180 |
| tacctgcaag ccagaggcct ggctgtgaag accatccaac agcacctggg ccagctcaac | 240 |
| atgctgcaca ggagatctgg cctgggtacc catactcttt atgcccccgg tggatatgac | 300 |
| attatgggat atctggacca gatcggcaac cggccaaacc cgcaggtgga actgggcccc | 360 |
| gtggatacat cctgcgcctt gattctttgt gacctgaaac agaaagacac cccgatagtt | 420 |
| tacgcgagtg aagccttcct ctacatgaca ggttacagca acgcagaggt gctgggccgg | 480 |
| aattgccggt ttctgcaaag ccctgacggc atggtgaagc ccagagcac ccggaagtac | 540 |
| gtggatagta acacaatcaa tactatgcgc aaggcaatcg acaggaatgc cgaggtgcag | 600 |
| gttgaagtag tcaattttaa aagaatgga cagcgatttg ttaatttcct gactatgata | 660 |
| cctgttaggg acgaaacagg cgagtatcga tactctatgg gattccagtg cgaaacagaa | 720 |
| ggcgaagcg tggcgtgcc caagaagaag aggaaagtcg gatccggcag cggcgccacc | 780 |
| aacttcagcc tgctgaagca ggccggcgac gtggaggaga ccccggcccc cctcgaggtg | 840 |
| cccaagaaga agaggaaagt cggcggacat actctttatg ccccggtgg atatgacatt | 900 |
| atgggatatc tgaggcagat caggaaccgg ccaaacccgc aggtggaact gggccccgtg | 960 |
| gatacatcct gcgccttgat tctttgtgac ctgaaacaga agacacccc gatagtttac | 1020 |
| gcgagtgaag ccttcctcta catgacaggt tacagcaacg cagaggtgct gggccggaat | 1080 |
| tgccggtttc tgcaaagccc tgacggcatg gtgaagccca gagcacccg aagtacgtg | 1140 |
| gatagtaaca caatcaatac tatgcgcaag gcaatcgaca ggaatgccga ggtgcaggtt | 1200 |
| gaagtagtca attttaaaaa gaatggacag cgatttgtta atttcctgac tatgataacct | 1260 |
| gttagggacg aaacaggcga gtatcgatac tctatgggat tccagtgcga aacagaaggt | 1320 |
| acccgccctt ctgactccaa tgctgtgtcc ctggtgatga ggagaatcag aaaggagaat | 1380 |
| gtggatgctg gggagagagc caagcaggcc ctggcctttg aacgcactga ctttgaccaa | 1440 |
| gtcagatccc tgatggagaa ctctgacaga tgccaggaca tcaggaacct ggccttcctg | 1500 |
| ggcattgcct acaacaccct gctgcgcatt gccgaaattg ccagaatcag agtgaaggac | 1560 |
| atctcccgca ccgatggtgg gagaatgctg atccacattg gcaggaccaa gacctggtg | 1620 |
| tccacagctg gtgtggagaa ggccctgtcc ctggggtta ccaagctggt ggagagatgg | 1680 |
| atctctgtgt ctggtgtggc tgatgacccc aacaactacc tgttctgccg ggtcagaaag | 1740 |
| aatggtgtgg ctgccccttc tgccacctcc caactgtcca ccggggccct ggaagggatc | 1800 |
| tttgaggcca cccaccgcct gatctatggt gccaaggatg actctgggca gagatacctg | 1860 |
| gcctggtctg gccactctgc cagagtgggt gctgccaggg acatggccag ggctggtgtg | 1920 |

```
tccatccctg aaatcatgca ggctggtggc tggaccaatg tgaacattgt gatgaactac    1980
atcagaaacc tggactctga gactggggcc atggtgaggc tgctcgaaga tggggac      2037
```

<210> SEQ ID NO 31

<400> SEQUENCE: 31

000

POLYPEPTIDE SET TO BE USED IN LIGHT DEPENDENT GENE RECOMBINATION

The content of the ASCII text file of the sequence listing named "Sequence_Listing.txt" which is 36,239 bytes in size was retrieved by the USPTO from the WIPO database and uploaded into the application file wrapper by the USPTO on Oct. 10, 2019 is incorporated herein by reference in its entirety.

TECHNICAL FIELD

The present invention relates to a set of polypeptides for use in light-dependent genetic recombination, and the like.

BACKGROUND ART

A genetic engineering technology making use of the Cre/loxP system is a powerful tool.

In the Cre/loxP system, a Cre protein, a recombinant enzyme, acts on a DNA sequence called "loxP sequence" and causes site-specific genetic recombination.

A Cre protein is an enzyme derived from bacteriophage P1 and has been used widely in the genetic engineering technology (Non-Patent Document 1).

There is known a control technology in the Cre/loxP system, which uses a split Cre obtained by splitting a Cre protein into two polypeptides and reconstitutes the activity in a light-dependent manner or in the presence of a drug.

More specifically, disclosed is a light-dependent control technology using CRY2-CreN and CIBN-CreC, a combination of the Cre/loxP system and a photo-switchable protein (Patent Document 1, Non-Patent Documents 2 and 3).

In addition, disclosed is a split-Cre-FRB/FKBP system as a technology of controlling genetic recombination in the presence of a drug (Non-Patent Documents 4 and 5).

In recent years, a molecular control approach making use of photoactivation of proteins has appeared and it is called optogenetics (Non-Patent Documents 6 and 7).

The present inventors modified a Vivid protein which is derived from *Neurospora crassa* and forms a homodimer in a light-dependent manner and developed a set of two proteins forming a dimer in a light-dependent manner which set is capable of precisely controlling the formation and dissociation of a dimer by illumination with a light (Patent Document 2 and Non-Patent Document 8. In addition, they developed, as a genom editing tool, a set of two polypeptides obtained by fusing fragments obtained by splitting, into two, Cas9 utilized in the CRISPR-Cas9 system with two polypeptides forming a dimer in a light-dependent manner or in the presence of a drug (Patent Document 3 and Non-Patent Document 9).

CITATION LIST

Patent Documents

Patent Document 1: WO2011/130540
Patent Document 2: Japanese Patent Application Laid-Open No. 2015-165776
Patent Document 3: WO2016/167300

Non-Patent Documents

Non-Patent Document 1: Meinke, G. et al., Chem. Rev. 116, 12785-12820 (2016)

Non-Patent Document 2: Kennedy, M. J., et al., Nat. Methods, 7(12), 973 (2010)
Non-Patent Document 3: Schindler S. E, et. al., Scientific Reports, 5, 13627 (2015)
Non-Patent Document 4: Jullien, N., et al., Nucleic Acids Research, 31(21), e131 (2003)
Non-Patent Document 5: Jullien, N., et al., PLoS One. 2(12), e1355 (2007)
Non-Patent Document 6: Toettcher, J. E. et al., Nat. Methods 8, 35-38 (2011).
Non-Patent Document 7: Mueller, K. et al., Mol. BioSyst. 9, 596-608 (2013).
Non-Patent Document 8: Kawano, F. et al., Nat. Commun. 6, 6256 (2015).
Non-Patent Document 9: Nihongaki, Y. et al., Nat. Biotech., 33, 755 (2015).

SUMMARY

Technical Problem

The technical problem of the present invention is to provide a novel polypeptide set for use in light-dependent genetic recombination, having a split Cre obtained by splitting a Cre protein into two polypeptides.

Solution to Problem

As a result of intensive investigation with a view to overcoming the above-described technical problem, the present inventors have found that it is possible to provide a set of polypeptides unexpectedly superior in genetic recombination activity to conventional light-dependently controlled split Cres by binding two proteins light-dependently forming a dimer to the respective specific sites of a split-Cre N-terminal side fragment (CreN) and C-terminal side fragment (CreC) obtained by splitting a Cre protein into two fragments and have completed the present invention.

The following are the present invention.

[1] A set of two polypeptides for use in light-dependent genetic recombination, in which an N-terminal side fragment and a C-terminal side fragment of a Cre protein having an amino acid sequence of SEQ ID NO: 1 respectively bind to two proteins light-dependently forming a dimer, the N-terminal side fragment and the C-terminal side fragment of the Cre protein are each a fragment having a cleavage site in a region of the amino acid sequence of SEQ ID NO: 1 between position 59 and position 68 or a fragment having a cleavage site in a region of the amino acid sequence of SEQ ID NO: 1 between position 101 and position 111;

the N-terminal side fragment of the Cre protein binds to, at a C-terminal amino acid thereof, and the C-terminal side fragment of the Cre protein binds to, at an N-terminal amino acid thereof, the two proteins light-dependently forming a dimer, respectively; and the two proteins light-dependently forming a dimer are each a polypeptide having an amino acid sequence of SEQ ID NO: 2 or a mutant thereof and in at least one of the proteins, at least one amino acid positioned at an N-terminal α helix has been substituted.

[2] The set of two polypeptides as described above in [1], wherein:

the N-terminal side fragment of the Cre protein has at least a region of the amino acid sequence of SEQ ID NO: 1 between position 19 and position 59 and the C-terminal side fragment of the Cre protein has at least a region of the amino acid sequence of SEQ ID NO: 1 between position 68 and position 343; or the N-terminal side fragment of the Cre protein has at least a region of the amino acid sequence of SEQ ID NO: 1 between position 19 and position 101 and the C-terminal side fragment of the Cre protein has at least a region of the amino acid sequence of SEQ ID NO: 1 between position 111 and position 343.

[3] The set of two polypeptides as described above in [1], wherein:

the N-terminal side fragment of the Cre protein has at least a region of the amino acid sequence of SEQ ID NO: 1 between position 19 and position 59 and the C-terminal side fragment of the Cre protein has at least a region of the amino acid sequence of SEQ ID NO: 1 between position 60 and position 343.

[4] The set of two polypeptides as described above in [1], wherein:

the N-terminal side fragment of the Cre protein has at least a region of the amino acid sequence of SEQ ID NO: 1 between position 19 and position 104 and the C-terminal side fragment of the Cre protein has at least a region of the amino acid sequence of SEQ ID NO: 1 between position 106 and position 343.

[5] The set of two polypeptides as described above in any of [1] to [4], wherein:

at least one of the N-terminal side fragment and the C-terminal side fragment of the Cre protein has, in a sequence thereof, addition, substitution, or deletion of one to several amino acids; or at least one of the fragments has a sequence having 80% or more sequence identity with the amino acid sequence of SEQ ID NO: 1 corresponding thereto.

[6] The set of two polypeptides as described above in any of [1] to [5], wherein:

at least an amino acid corresponding to position 52 and/or position 55 of SEQ ID NO: 2 in one of the two proteins light-dependently forming a dimer has been substituted with lysine, arginine or histidine and at least an amino acid corresponding to position 52 and/or position 55 of SEQ ID NO: 2 in the other one of the two proteins light-dependently forming a dimer has been substituted with aspartic acid, glutamic acid, or glycine.

[7] The set of two polypeptides as described above in [6], wherein:

the two proteins light-dependently forming a dimer are a combination of pMag, pMagHigh1, pMagFast1, or pMagFast2 and nMag, nMagHigh1, nMagFast1, or nMagFast2.

[8] The set of two polypeptides as described above in any of [1] to [7], wherein:

the N-terminal side fragment and the C-terminal side fragment of the Cre protein bind to the two proteins light-dependently forming a dimer, respectively, via a linker.

[9] The set of two polypeptides as described above in any of [1] to [8], wherein:

a nuclear localization signal sequence binds to a C-terminal amino acid of one of the proteins light-dependently forming a dimer which is to be bound to the N-terminal side fragment of the Cre protein and/or to an N-terminal amino acid of the other protein light-dependently forming a dimer which is to be bound to the C-terminal side fragment of the Cre protein, via a linker or a without a linker.

[10] The set of two polypeptides as described above in any of [1] to [9], further including a 2A peptide sequence.

[11] The set of two polypeptides as described above in any of [1] to [10], wherein:

one of the two polypeptides of the set has, from the N-terminal side to the C-terminal side thereof, the following amino acid sequences in order of mention: the N-terminal side fragment of the Cre protein, one of the proteins light-dependently forming a dimer, the nuclear localization signal sequence, and a portion of the 2A peptide sequence; and the other polypeptide has, from the N-terminal side to the C-terminal side thereof, the following amino acid sequences in order of mention: a portion of the 2A peptide sequence, the nuclear localization signal sequence, the other protein light-dependently forming a dimer, and the C-terminal side fragment of the Cre protein.

[12] The set of two polypeptides as described above in [11], wherein:

binding between the N-terminal side fragment of the Cre protein and one of the proteins light-dependently forming a dimer, binding between the one of the proteins light-dependently forming a dimer and the nuclear localization signal sequence, binding between the nuclear localization signal sequence and the portion of the 2A peptide sequence, binding between the portion of the 2A peptide sequence and the nuclear localization signal sequence, binding between the nuclear localization signal sequence and the other protein light-dependently forming a dimer, and binding between the other protein light-dependently forming a dimer and the C-terminal side fragment of the Cre protein are each binding via a linker.

[13] A nucleic acid encoding the set of two polypeptides as described above in any of [1] to [12].

[14] The nucleic acid as described above in [13], encoding a polypeptide having amino acid sequences in the following order: the N-terminal side fragment of the Cre protein, one of the proteins light-dependently forming a dimer, the nuclear localization signal sequence, the 2A peptide sequence, the nuclear localization signal sequence, the other protein light-dependently forming a dimer, the C-terminal side fragment of the Cre protein.

[15] An expression vector including the nucleic acid as described above in [13] or [14].

[16] A Cre-loxP system, including the set of two polypeptides as described above in any of [1] to [12], the nucleic acid as described above in [13] or [14] or the expression vector as described above in [15], and a nucleic acid having a loxP sequence or a loxP mutant sequence.

[17] The Cre-loxP system as described above in [16], wherein:

the loxP mutant is selected from the group consisting of lox2722, lox66, lox71, JT15, and JTZ17.

[18] An animal having the set of two polypeptides as described above in any of [1] to [12], the nucleic acid as described above in [13] or [14], the expression vector as described above in [15], or the Cre-loxP system as described above in [16] or [17].

[19] The animal as described above in [18], which is a rodent.

Advantage of the Invention

The present invention makes it possible to provide a novel set of polypeptides for use in light-dependent genetic recombination, having a split Cre obtained by splitting a Cre protein into two polypeptides.

BRIEF DESCRIPTION OF DRAWINGS

FIG. 5 shows the respective base sequences of loxP and lox2722, lox66, lox71, JT15, and JTZ17 which are loxP mutants (corresponding to the base sequences of SEQ ID NOS: 7 to 12 in this order, respectively). lox72 (SEQ ID NO: 13) is a product obtained by DNA recombination between lox66 and lox71 and JA15-JTZ17 (SEQ ID NO: 14) is a product obtained by DNA recombination between JT15 and JTZ17.

FIG. 14 shows the amino acid sequence of PA-Cre of the present invention when the Cre protein is cleaved between the 59th amino acid and the 60th amino acid. The top sequence is SEQ ID NO: 25 and the bottom sequence is SEQ ID NO: 26.

FIG. 15 shows the amino acid sequence of PA-Cre of the present invention when the Cre protein is cleaved between the 104th amino acid and the 106th amino acid. The top sequence is SEQ ID NO: 27 and the bottom sequence is SEQ ID NO: 28.

FIG. 16 shows a base sequence (SEQ ID NO: 29) to be inserted in a vector of PA-Cre of the present invention when the Cre protein is cleaved between the 59th amino acid and the 60th amino acid.

FIG. 17 shows a base sequence (SEQ ID NO: 30) to be inserted in a vector of PA-Cre of the present invention when the Cre protein is cleaved between the 104th amino acid and the 106th amino acid.

DESCRIPTION OF EMBODIMENTS

Figure 1:
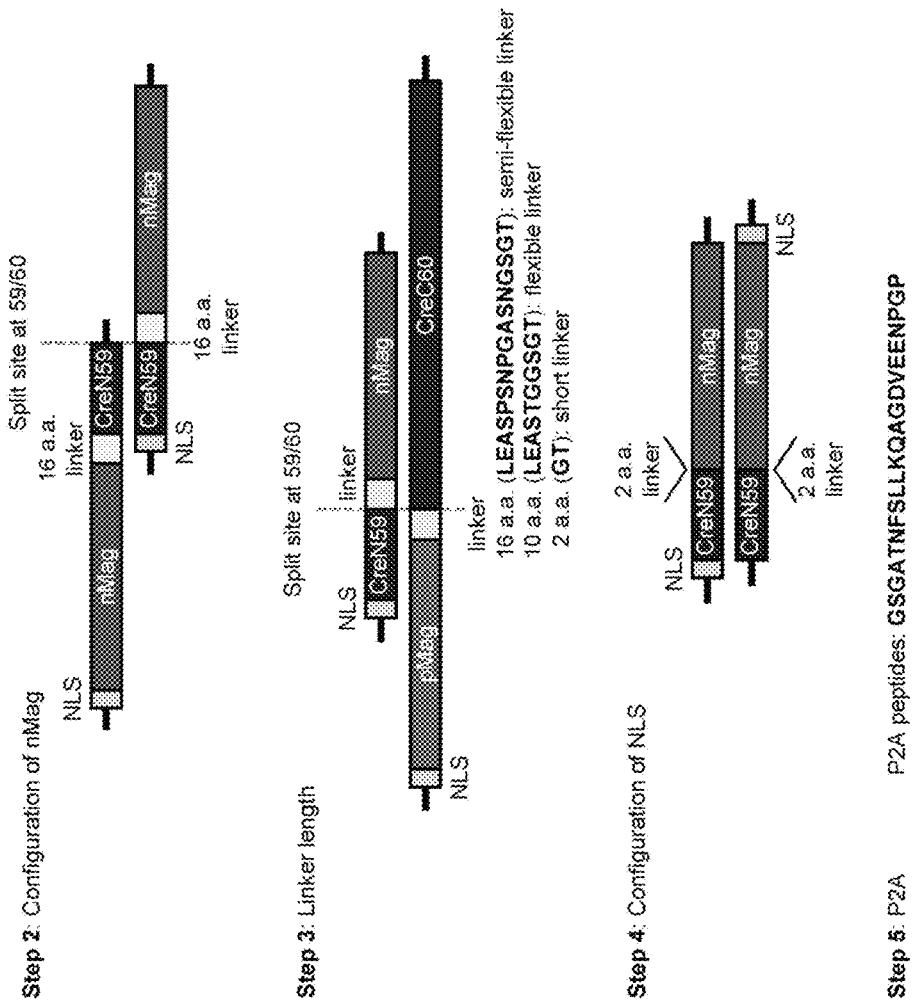
FIG. 1 is a conceptual diagram of a construct of a polypeptide set for use in light-dependent genetic recombination according to the present invention (which may hereinafter be called "PA-Cre: photo-activatable Cre recombinase"). (Step 2) shows a construct in which nMag is bound to the N-terminal amino acid of CreN59 and a construct in which nMag is bound to the C-terminal amino acid of CreN59. The CreN and CreC respectively represent the N-terminal side fragment and the C-terminal side fragment of a split Cre obtained by splitting a Cre protein into two. The CreN59 represents the N-terminal side fragment having a region of the amino acid sequence of SEQ ID NO: 1 between position 19 and position 59, while CreC60 represents the C-terminal side fragment having a region of the amino acid sequence of SEQ ID NO: 1 between position 60 and position 343. The pMag and nMag are two proteins light-dependently forming a dimer; and NLS is a nuclear localization signal sequence. (Step 3) shows a construct in which nMag is bound to the C terminal amino acid of CreN59 via a linker and a construct in which CreC60 is bound to the C-terminal amino acid of pMag via a linker, the linker having three kinds (SEQ ID NOS: 3 to 5) of length (16 a.a., 19 a.a., and 2 a.a.). (Step 4) shows a construct in which a nuclear localization signal sequence (NLS) is bound to the N-terminal amino acid of CreN59 and a construct in which a nuclear localization signal sequence is bound to the C-terminal amino acid of nMag. (Step 5) shows an amino acid sequence (P2A peptide sequence, SEQ ID NO: 6) of a P2A peptide used as a 2A peptide.

The present invention will be described specifically by some modes for carrying out the invention. The present invention is not limited to the following modes for carrying out the invention but can be carried out after being modified in various ways.

The set of two polypeptides according to the present invention is a set of two polypeptides for use in light-dependent genetic recombination, in which an N-terminal side fragment and a C-terminal side fragment of a Cre protein having an amino acid sequence of SEQ ID NO: 1 respectively bind to two proteins light-dependently forming a dimer, wherein:
  the N-terminal side fragment and the C-terminal side fragment of the Cre protein are each a fragment having a cleavage site in a region of the amino acid sequence of SEQ ID NO: 1 between position 59 and position 68 or a fragment having a cleavage site in a region of the amino acid sequence of SEQ ID NO: 1 between position 101 and position 111;
  the N-terminal side fragment of the Cre protein binds to, at the C-terminal amino acid thereof, and the C-terminal side fragment of the Cre protein binds to, at the N-terminal amino acid thereof, the two proteins light-dependently forming a dimer, respectively; and
  the two proteins light-dependently forming a dimer are each a polypeptide having an amino acid sequence of SEQ ID NO: 2 or a mutant thereof and in at least one of the proteins, at least one amino acid positioned at an N-terminal α helix has been substituted.

In other words, the N-terminal side fragment of the Cre protein binds, at the C-terminal amino acid thereof, to one of the two proteins light-dependently forming a dimer and the C-terminal side fragment of the Cre protein binds, at the N-terminal amino acid thereof, to the other one of the two Magnet proteins light-dependently forming a dimer.

In the set of two polypeptides according to the present invention, since the two proteins light-dependently forming a dimer form a dimer by illumination with a light, the N-terminal side fragment of the Cre protein and the C-terminal side fragment of the Cre protein that bind to two proteins light-dependently forming a dimer are reassembled into the Cre protein and thus recover the recombinase activity of the Cre protein. The set of two polypeptides according to the present invention can therefore be used for light-dependent genetic recombination.

The term "for use in genetic recombination" as used herein means for use in a genetic recombination technology based on the Cre/loxP system.

In the present invention, the Cre protein has an amino acid sequence represented by SEQ ID NO: 1 and has a cleavage site in a region of the amino acid sequence of SEQ ID NO: 1 between position 59 and position 68 or in a region of the amino acid sequence of SEQ ID NO: 1 between position 101 and position 111. By cleavage of the Cre protein in either of these regions, two split Cre fragments are formed. Of the two fragments thus obtained by cleavage, an N-terminal side fragment of SEQ ID NO: 1 is called "N-terminal side fragment (CreN) of the Cre protein", while a C-terminal side fragment is called "C-terminal side fragment (CreC) of the Cre protein".

Described specifically, in the present invention, when the amino acid sequence of the N-terminal side fragment of the Cre protein is compared with the amino acid sequence of the C-terminal side fragment of the Cre protein, the N-terminal side fragment of the Cre protein has an amino acid sequence in a region, in SEQ ID NO: 1, nearer to the N-terminal side than the C-terminal side fragment of the Cre protein. The C-terminal amino acid of the N-terminal side fragment of the Cre protein is an amino acid on the side nearer to the N-terminal side than the N-terminal amino acid of the C-terminal side fragment in the sequence of SEQ ID NO: 1.

The N-terminal side fragment and the C-terminal side fragment of the Cre protein may each be a fragment having a partial sequence of the Cre protein or having a sequence including, in the partial sequence, mutation.

The term "a fragment having a partial sequence of the Cre protein" means a fragment having, when the Cre protein having an amino acid sequence of SEQ ID NO: 1 is cleaved, a partial sequence of the amino acid sequence of SEQ ID NO: 1 from the N-terminal amino acid to the amino acid at the cleavage site, or a fragment having a partial sequence of the amino acid sequence of SEQ ID NO: 1 from the amino acid at the cleavage site to the C-terminal amino acid.

When the N-terminal side fragment and the C-terminal side fragment of the Cre protein having an amino acid sequence of SEQ ID NO: 1 are fragments having a partial sequence, these fragments are not required to have the N-terminal amino acid of the amino acid sequence of SEQ ID NO: 1 and/or the C-terminal amino acid of the amino acid sequence of SEQ ID NO: 1.

The N-terminal side fragment and the C-terminal side fragment of the Cre protein having an amino acid sequence of SEQ ID NO: 1, may have, in the amino acid sequence of SEQ ID NO: 1, a sequence including mutation or may have, in the partial sequence of the Cre protein, a sequence including mutation.

In the set of two polypeptides according to the present invention, the N-terminal side fragment and the C-terminal side fragment of the Cre protein having an amino acid sequence of SEQ ID NO: 1 may have, in the respective amino acid sequences thereof, an amino acid sequence having 100% homology with the amino acid sequence of SEQ ID NO: 1; or may have an amino acid sequence obtained by mutation of the amino acid sequence of SEQ ID NO: 1. Each fragment may have an amino acid sequence which is a partial sequence of the amino acid sequence of SEQ ID NO: 1 or an amino acid sequence obtained by mutation of the amino acid sequence which is a partial sequence of the amino acid sequence of SEQ ID NO: 1.

The N-terminal side fragment and the C-terminal side fragment of the Cre protein, may be cleaved at the C terminal of the N-terminal side fragment and the N terminal of the C-terminal side fragment; or may be cleaved so as to delete from one to several amino acids connecting the C terminal of the N-terminal side fragment and the N terminal of the C-terminal side fragment.

Figure 4:
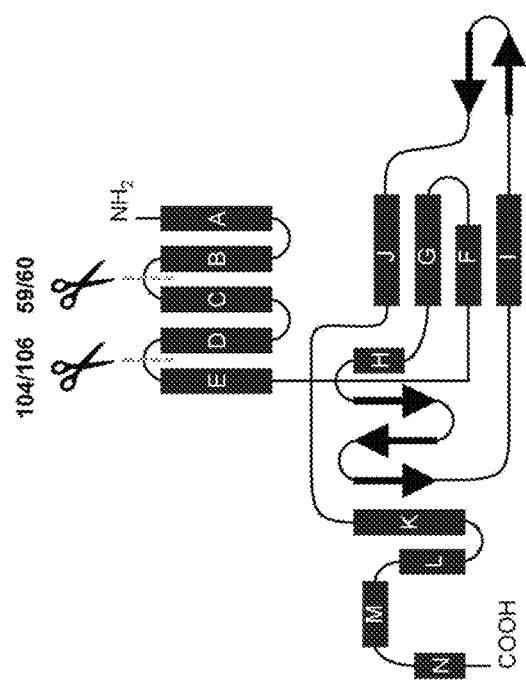
FIG. 4 shows the secondary structure of the Cre protein and a cleavage site in Example. Cleavage between the 59th amino acid and the 60th amino acid (59/60) and cleavage between the 104th amino acid and the 106th amino acid are given as examples.

The Cre protein is known to have a secondary structure as shown in FIG. 4.

Amino acids of the amino acid sequence of SEQ ID NO: 1 from position 59 to position 68 correspond to amino acids present between B-α-helix and C-α-helix of the Cre protein, while amino acids of the amino acid sequence of SEQ ID NO: 1 from position 101 to position 111 correspond to amino acids between D-α-helix and E-α-helix of the Cre protein.

Amino acids of the amino acid sequence of SEQ ID NO: 1 from position 59 to position 68 and amino acids of the amino acid sequence of SEQ ID NO: 1 from position 101 to position 111 are regions which are revealed by the results of crystal structure analysis (Guo, F., et al., Nature, 389, 40-46 (1997)) to have a flexible loop structure between a helixes.

The term, "the N-terminal side fragment and the C-terminal side fragment, of the Cre protein, are each a fragment having a cleavage site in a region of the amino acid sequence of SEQ ID NO: 1 between position 59 and position 68" means that it may have a cleavage side in a region of the amino acid sequence of SEQ ID NO: 1 between position 59 and position 68. The N-terminal side fragment of the Cre protein is a fragment containing at least an amino acid sequence up to the amino acid at position 59 and the C-terminal side fragment of the Cre protein is a fragment containing at least an amino acid sequence including and following the amino acid at position 68.

The term, "the N-terminal side fragment and the C-terminal side fragment of the Cre protein are each a fragment having a cleavage site in a region of the amino acid sequence of SEQ ID NO: 1 between position 101 and position 111" means that it may have a cleavage side in a region of the amino acid sequence of SEQ ID NO: 1 between position 101 and position 111. The N-terminal side fragment of the Cre protein is a fragment containing at least an amino acid sequence up to the amino acid at position 101 and the C-terminal side fragment of the Cre protein is a fragment containing at least an amino acid sequence including and following the amino acid at position 111.

The N-terminal side fragment and the C-terminal side fragment of the Cre protein may be designed to include regions of the amino acid sequence of SEQ ID NO: 1 between position 1 and position 59 and between position 68 and position 343 or regions of the amino acid sequence of SEQ ID NO: 1 between position 1 and position 101 and between position 111 and position 343, respectively.

The N-terminal amino acid in the N-terminal side fragment of the Cre protein and the C-terminal amino acid in the C-terminal side fragment of the Cre protein are not particularly limited in the amino acid sequence of SEQ ID NO: 1 insofar as the N-terminal side fragment and the C-terminal side fragment can light-dependently recover genetic recombination activity.

In designing so as to include respective regions of the amino acid sequence of SEQ ID NO: 1 between position 1 and position 59 and between position 68 and position 343, the N-terminal side fragment and the C-terminal side fragment of the Cre protein may have partial sequences in the regions of the amino acid sequence of SEQ ID NO: 1 between position 1 and position 59 and between position 68 and position 343, respectively without particular limitation insofar as the split Cre when dimerized still keeps the recombinase activity of the Cre protein. The N-terminal side fragment and the C-terminal side fragment of the Cre protein may have, in the respective regions of the amino acid sequence of SEQ ID NO: 1 between position 1 and position 59 and between position 68 and position 343, mutation in the amino acid sequence; or may be fragments having mutation and at the same time, having the partial sequence.

Either of the N-terminal side fragment or the C-terminal side fragment of the Cre protein may have all or some of the amino acids in the region of the amino acid sequence of SEQ ID NO: 1 between position 60 and position 67. When the N-terminal side fragment and the C-terminal side fragment of the Cre protein have some or all of the amino acids in the region between position 60 and position 67, the amino acid sequence in the region between position 60 and position 67 may have mutation.

In designing so as to include respective regions of the amino acid sequence of SEQ ID NO: 1 between position 1 and position 101 and between position 111 and position 343, the N-terminal side fragment and the C-terminal side fragment of the Cre protein may have partial sequences in the regions of the amino acid sequence of SEQ ID NO: 1 between position 1 and position 101 and between position 111 and position 343 without particular limitation insofar as the split Cre when dimerized still keeps recombinase activity of the Cre protein. The N-terminal side fragment and the C-terminal side fragment of the Cre protein may have, in the respective regions of the amino acid sequence of SEQ ID NO: 1 between position 1 and position 101 and between position 111 and position 343, mutation in the amino acid sequence; or may be fragments having mutation and having the partial sequence.

Either of the N-terminal side fragment or the C-terminal side fragment of the Cre protein may have all or some of the amino acids in the region of the amino acid sequence of SEQ ID NO: 1 between position 102 and position 110. When the N-terminal side fragment and the C-terminal side fragment of the Cre protein have some or all of the amino acids in the region between position 102 and position 110, the amino acid sequence in the region between position 102 and position 110 may have mutation.

When the N-terminal side fragment and the C-terminal side fragment of the Cre protein are each a fragment having a partial sequence, the C-terminal amino acid of the N-terminal side fragment of the Cre protein and the N-terminal amino acid of the C-terminal side fragment are preferably amino acids at a cleavage site, respectively.

In the polypeptide set of the present invention, it is preferred that the N-terminal side fragment of the Cre protein has at least a region of the amino acid sequence of SEQ ID NO: 1 between position 19 and position 59 and the C-terminal side fragment of the Cre protein has at least a region of the amino acid sequence of SEQ ID NO: 1 between position 68 and position 343; or the N-terminal side fragment of the Cre protein has at least a region of the amino acid sequence of SEQ ID NO: 1 between position 19 and position 101 and the C-terminal side fragment of the Cre protein has at least a region of the amino acid sequence of SEQ ID NO: 1 between position 111 and position 343.

In the polypeptide set of the present invention, it is more preferred that the N-terminal side fragment of the Cre protein has at least a region of the amino acid sequence of SEQ ID NO: 1 between position 19 and position 59 and the C-terminal side fragment of the Cre protein has at least a region of the amino acid sequence of SEQ ID NO: 1 between position 60 and position 343; or the N-terminal side fragment of the Cre protein has at least a region of the amino acid sequence of SEQ ID NO: 1 between position 19 and position 104 and the C-terminal side fragment of the Cre protein has at least a region of the amino acid sequence of SEQ ID NO: 1 between position 106 and position 343.

The N-terminal side fragment and the C-terminal side fragment may be designed so that a region overlapping with the amino acid sequence of SEQ ID NO: 1 becomes 70% or more, 80% or more, 90% or more, 95% or more, 98% or more, 100%, or 100% or more of the amino acid sequence of SEQ ID NO: 1. For example, when the N-terminal side fragment is comprised of from the amino acid at position 19 to the amino acid at position 59 of SEQ ID NO: 1 and the C-terminal side fragment is comprised of from the amino acid at position 60 to the amino acid at position 343, they have 325 amino acids in total, that is, 41 amino acids from the amino acid at position 19 to the amino acid at position 59 and 284 amino acids from the amino acid at position 60 to the amino acid at position 343. This means that 325/343, that is, about 95% of the amino acid sequence of SEQ ID NO: 1 becomes an overlapping region. For example, when the N-terminal side fragment is comprised of from the amino acid at position 19 to the amino acid at position 104 of SEQ ID NO: 1 and the C-terminal side fragment is comprised of from the amino acid at position 106 to the amino acid at position 343, the protein has 324 amino acids in total, that is, 86 amino acids from position 19 to position 104 and 238 amino acids from position 106 to position 343. This means that 324/343, that is, about 94% of the amino acid sequence of SEQ ID NO: 1 becomes an overlapping region.

In the present specification, the "overlapping region of the N-terminal side fragment and/or C-terminal side fragment with the amino acid sequence of SEQ ID NO: 1" can be determined by aligning their amino acids so as make them coincide with each other as much as possible by a method known to those skilled in the art and finding the percentage of amino acids overlapping with 343 amino acids of the Cre protein.

In the present specification, this method can also be applied to the following fragments: "a fragment having an amino acid sequence obtained by addition, substitution, or deletion of one to several amino acids from the amino acid sequence of SEQ ID NO: 1" or "a fragment having an amino acid sequence having 80% or more sequence identity to the amino acid sequence of SEQ ID NO: 1".

When the N-terminal side fragment is comprised of from the amino acid at position 19 to the amino acid at position 59 of SEQ ID NO: 1 and the C-terminal side fragment is comprised of from the amino acid at position 60 to the amino acid at position 343 and they have, for example, addition, substitution, or deletion of from one to nine amino acids, from 324/343 (about 94%) to 316/343 (about 92%) becomes an overlapping region as a result of the alignment. When the N-terminal side fragment has from an amino acid at position 19 to an amino acid at position 104 of SEQ ID NO: 1 and the C-terminal side fragment has from an amino acid at position 106 to an amino acid at position 343 and they have, for example, addition, substitution, or deletion of from one to nine amino acids, from 323/343 (about 94%) to 315/343 (about 92%) becomes an overlapping region as a result of the alignment.

The N-terminal side fragment and the C-terminal side fragment of the Cre protein may be any of the following combinations:

a combination of, as the N-terminal side fragment and the C-terminal side fragment of the Cre protein, fragments each having a cleavage site in a region of the amino acid sequence of SEQ ID NO: 1 between position 59 and position 68;

a combination of, as the N-terminal side fragment and the C-terminal side fragment of the Cre protein, fragments each having a cleavage site in a region of the amino acid sequence of SEQ ID NO: 1 between position 101 and position 111;

a combination of, as the N-terminal side fragment and the C-terminal side fragment, a fragment comprised of amino acids from position 19 to position 59 and a fragment comprised of amino acids from position 60 to position 343, each of the amino acid sequence of SEQ ID NO: 1, respectively;

a combination of, as the N-terminal side fragment and the C-terminal side fragment, a fragment comprised of amino acids from position 19 to position 104 and a fragment comprised of amino acids from position 106 to position 343, each of the amino acid sequence of SEQ ID NO: 1, respectively;

any of the above-described combinations including, in the sequence of at least one of the fragments, addition, substitution, or deletion of one to several amino acids;

any of the above-described combinations including, in the respective sequences of the two fragments, addition, substitution, or deletion of one to several amino acids;

any of the above-described combinations having, as the sequence of at least one of the fragments, a sequence having 80% or more sequence identity with the above-described sequence; and any of the above-described combinations having, as the respective sequences of the two fragments, a sequence having 80% or more sequence identity with the above-described sequence.

In the present specification, the term "amino acid" is used in its broadest meaning and it embraces not only naturally occurring amino acids but also derivatives thereof and artificial amino acids. Examples of the "amino acid" used herein include naturally occurring proteinogenic L-amino acids, non-naturally occurring amino acids, and chemically synthesized compounds having properties known in the art as characteristics of an amino acid.

Examples of the non-naturally occurring amino acids include, but are not limited to, α,α-disubstituted amino acids (such as α-methylalanine), N-alkyl-α-amino acids, D-amino acids, δ-amino acids, and α-hydroxy acids, each having a main chain structure different from that of the naturally occurring type; amino acids (such as norleucine and homohistidine) having a side-chain structure different from that of the naturally occurring type; amino acids (such as "homo" amino acids, homophenylalanine, and homohistidine) having extra methylene on the side chain thereof; and amino acids (such as cysteic acid) obtained by substituting a carboxylic acid functional group amino acid on the side chain by a sulfonic acid group.

In the present specification, an amino acid is sometimes represented by a commonly used single-letter or three-letter code. The amino acid represented by a single-letter or three-letter code may include a mutant or a derivative thereof.

When the term "having addition, substitution, or deletion of one to several amino acids from a certain amino acid sequence" is used herein, 1, 2, 3, 4, 5, 6, 7, 8, or 9 amino acids have been added (inserted), substituted, or deleted at an end or non-end of the sequence. The number of amino acids to be added, substituted or deleted is not particularly limited insofar as the resulting polypeptide exhibits its effect of the present invention. The number of sites added, substituted, or deleted may be either one or two or more.

The term "having 80% or more sequence identity with a certain amino acid sequence" as used herein means that sequence identity may be 85% or more, 90% or more, 95% or more, 98% more, or 99% or more. The sequence identity can be determined by alignment based on a method known to those skilled in the art.

The set of two polypeptides according to the present invention shows light-dependent genetic recombination activity. By using a loxP sequence or a loxP mutant sequence in combination, genetic recombination can be carried out light dependently.

(Two Proteins Light-Dependently Forming a Dimer)

The term "two proteins light-dependently forming a dimer" (which may hereinafter be called "magnet") as used herein means a pair of proteins forming a heterodimer when illuminated with a light. The magnet forms a heterodimer when illuminated with a light, preferably, a blue light, while the heterodimer rapidly dissociates by stopping the illumination with a light. Thus, it can precisely control the formation and dissociation of a dimer in the set of two polypeptides according to the present invention and thereby allows the Cre protein to recover its recombinase activity light dependently.

In the set of two respectively different polypeptides according to the present invention, two proteins light-dependently forming a dimer are each a polypeptide having an amino acid sequence of SEQ ID NO: 2 or a mutant thereof and in at least one of the proteins, at least one amino acid positioned at the N-terminal α helix has been substituted.

In the present invention, the magnet is derived from polypeptides each having an amino acid sequence of SEQ ID NO: 2 or a mutant thereof. In other words, the polypeptide having an amino acid sequence of SEQ ID NO: 2 is a Vivid protein and the mutant of the polypeptide having an amino acid sequence of SEQ ID NO: 2 is a mutant of a Vivid protein.

The mutant of a Vivid protein may be, for example, a protein having 70% or more, 75% or more, 80% or more, 85% or more, 90% or more, 95% or more, 98% more, or 99% or more sequence identity with the amino acid sequence of SEQ ID NO: 2.

The magnet may be any of a pair of a Vivid protein and a Vivid protein, a pair of a Vivid protein and a mutant of a Vivid protein, and a pair of a mutant of a Vivid protein and a mutant of a Vivid protein. In at least one of the polypeptides of the pair, at least one amino acid positioned at the N-terminal α helix has been substituted.

In the present specification, a mutant of a Vivid protein is a polypeptide having, at a position other than the N-terminal α helix, a sequence different from the amino acid sequence of SEQ ID NO: 2. The mutant of a Vivid protein may be an N-terminal cleaved polypeptide (polypeptide made of amino acids from position 37 to position 186 of the amino acid sequence of SEQ ID NO: 2).

The number of amino acids substituted at the N-terminal α helix in the magnet is not limited insofar as a desired dimer formation efficiency and dissociation rate can be achieved. The number of the amino acids substituted can be set at, for example, 1, 2, 3, 4, 5, 6, 7, 8, 9, or 10. When two or more amino acids are substituted, they may be the same or different from each other.

As the N-terminal α helix, amino acids at positions from 47 to 56 of SEQ. ID NO: 2 are preferred. It is preferred that in at least one of the two proteins light-dependently forming a dimer according to the present invention, at least one of the amino acids at positions from 47 to 56 of SEQ ID NO: 2 has been substituted; and is more preferred that in the two proteins, at least one of the amino acids at positions from 47 to 56 of SEQ ID NO: 2 has been substituted.

The mutation in the N-terminal α helix is preferably mutation in at least one of the amino acids at positions 47, 48, 50, 51, 52, 54, and 55 of SEQ ID NO: 2.

It is preferred that in one of the proteins of the magnet, at least one amino acid of the N-terminal α helix has been substituted with an amino acid having, on a side chain thereof, a positive charge and in the other protein of the magnet, at least one amino acid of the N-terminal α helix has been substituted with an amino acid having, on the side chain thereof, a negative charge. Such a constitution enhances affinity of the two proteins of the magnet, thereby making it possible to achieve improvement in dimer formation efficiency.

The amino acid having, on the side chain thereof, a positive charge may be either a naturally occurring amino acid or a non-naturally occurring amino acid. Examples of the naturally occurring amino acid include lysine, arginine, and histidine. The amino acid having, on the side chain thereof, a negative charge may be either a naturally occurring amino acid or a non-naturally occurring amino acid. Examples of the naturally occurring amino acid include aspartic acid and glutamic acid.

It is preferred that in at least one of the proteins of the magnet, an amino acid corresponding to position 52 and/or an amino acid corresponding to position 55, each of SEQ ID NO: 2, has been substituted; and is more preferred that in the two proteins of the magnet, an amino acid corresponding to position 52 and/or an amino acid corresponding to position 55, each of SEQ ID NO: 2 has been substituted.

The amino acids corresponding to position 52 and position 55 of SEQ ID NO: 2 may be substituted, respectively, with the same amino acid or amino acids different from each other.

The term "amino acid corresponding to position X of SEQ ID NO: 2" as used herein means an amino acid at position X of SEQ ID NO: 2 when two proteins constituting the magnet have an amino acid sequence same as SEQ ID NO: 2 before substitution of an amino acid.

When two proteins constituting the magnet have an amino acid sequence different from SEQ ID NO: 2 before substitution of an amino acid, more specifically, when it is a mutant of a Vivid protein, it means an amino acid corresponding to position X of SEQ ID NO: 2.

The "amino acid at position X of SEQ ID NO: 2" in the mutant is determined as needed by the alignment of the sequence or the like.

It is preferred that in at least one of the proteins of the magnet, the amino acid corresponding to position 52 of SEQ ID NO: 2 has been substituted with an amino acid having, on the side chain thereof, a positive charge. If desired, it is more preferred that in the other protein, the amino acid corresponding to position 52 of SEQ ID NO: 2 has been substituted with an amino acid having, on the side chain thereof, a negative charge or a neutral amino acid, with substitution with an amino acid having, on the side chain thereof, a negative charge being further more preferred.

It is preferred that in at least one of the proteins of the magnet, the amino acid corresponding to position 55 of SEQ ID NO: 2 has been substituted with an amino acid having, on the side chain thereof, a positive charge. If desired, it is more preferred that in the other protein, the amino acid corresponding to position 55 of SEQ ID NO: 2 has been substituted with an amino acid having, on the side chain thereof, a negative charge or a neutral amino acid, with substitution with an amino acid having, on the side chain thereof, a negative charge being further more preferred.

It is preferred that in at least one of the proteins of the magnet, the amino acids corresponding to positions 52 and 55 of SEQ ID NO: 2 have been substituted, respectively, with the same or different amino acids having, on the side chain thereof, a positive charge. If desired, it is more preferred that in the other protein, the amino acids corresponding to positions 52 and 55 of SEQ ID NO: 2 have been substituted, respectively, with the same or different amino acids having, on the side chain thereof, a negative charge or neutral amino acids. When in one of the proteins of the magnet, the amino acids corresponding to positions 52 and 55 of SEQ ID NO: 2 have been substituted, respectively, with amino acids having, on the side chain thereof, a negative charge or neutral amino acids, it is preferred that the substituents are different from each other; is more preferred that one of the amino acids has been substituted with an amino acid having, on the side chain thereof, a negative charge and the other amino acid has been substituted with a neutral amino acid; and is further more preferred that the amino acid corresponding to position 52 of SEQ ID NO: 2 has been substituted with an amino acid having, on the side chain thereof, a negative charge and the amino acid corresponding to position 55 of SEQ ID NO: 2 has been substituted with a neutral amino acid.

When the amino acids corresponding to position 52 and/or position 55 of SEQ ID NO: 2 have been substituted, respectively, with amino acids having, on the side chain thereof, a positive charge, they have been substituted with the same or different substituents, preferably with lysine, arginine, or histidine, more preferably with arginine.

When the amino acids corresponding to position 52 and/or position 55 of SEQ ID NO: 2 have been substituted, respectively, with amino acids having, on the side chain thereof, a negative charge, they have been substituted with the same or different substituents, preferably with aspartic acid or glutamic acid, more preferably with aspartic acid.

When the amino acids corresponding to position 52 and/or position 55 of SEQ ID NO: 2 have been substituted with a neutral amino acid, they have been substituted preferably with glycine.

The amino acid corresponding to position 52 of SEQ ID NO: 2 has been substituted preferably with aspartic acid or glutamic acid, more preferably with aspartic acid. At the same time, the amino acid corresponding to position 55 of SEQ ID NO: 2 has been substituted preferably with a neutral amino acid, more preferably with glycine.

More specifically, one of the proteins of the magnet has a sequence obtained by substituting Ile at position 52 and Met at position 55 with an amino acid having, on the side chain thereof, a positive charge and the other protein of the magnet has a sequence obtained by substituting Ile at position 52 and Met at position 55 with an amino acid having, on the side chain thereof, a negative charge and/or a neutral amino acid.

As the magnet, usable are two proteins developed by the present inventors based on a Vivid protein and disclosed in Japanese Patent Application Laid-Open No. 2015-165776.

The following are specific examples of the magnet.

Examples of the one of the proteins of the magnet having a sequence obtained by substituting Ile at position 52 and Met at position 55 with an amino acid having, on the side chain thereof, a positive charge include pMag, pMagHigh1, pMagFast1, and pMagFast2, while examples of the other protein of the magnet having a sequence obtained by substituting Ile at position 52 and Met at position 55 with an amino acid having, on the side chain thereof, a negative charge and/or a neutral amino acid include nMag, nMagHigh1, nMagFast1, and nMagFast2.

The magnet is preferably a combination of one protein selected from pMag, pMagHigh1, pMagFast1, and pMagFast2 and one protein selected from nMag, nMagHigh1, nMagFast1, and nMagFast2.

In the present specification, pMag is a polypeptide having an amino acid sequence of SEQ ID NO: 15 and having mutations of I52R and M55R and pMagHigh1 is a polypeptide having an amino acid sequence of SEQ ID NO: 16 and having further mutations of M135I and M165I in the amino acid sequence of pMag. pMagFast1 is a polypeptide having an amino acid sequence of SEQ ID NO: 17 and having a further mutation of I85V in the amino acid sequence of pMag. pMagFast2 is a polypeptide having an amino acid sequence of SEQ ID NO: 18 and having further mutations of I74V and I85V in the amino acid sequence of pMag.

In the present specification, nMag is a polypeptide having an amino acid sequence of SEQ ID NO: 19 and having mutations of I52D and M55G and nMagHigh1 is a polypeptide having an amino acid sequence of SEQ ID NO: 20 and having further mutations of M135I and M165I in the amino acid sequence of nMag. nMagFast1 is a polypeptide having an amino acid sequence of SEQ ID NO: 21 and having a further mutation of I85V in the amino acid sequence of nMag. nMagFast2 is a polypeptide having an amino acid sequence of SEQ ID NO: 22 and having further mutations of I74V and I85V in the amino acid sequence of nMag.

The respective polypeptides of the magnet can be bound to the N-terminal side fragment and the C-terminal side fragment of the Cre protein, respectively, by a known method. Examples include a method of linking nucleic acids respectively encoding them as needed and causing to express them as fusion polypeptides. In this case, a polypeptide which will be a linker may be interposed between either one of the polypeptides of the magnet and the N-terminal side fragment or the C-terminal side fragment.

In the present invention, although a linker may be interposed, the polypeptides of the magnet are linked to the C-terminal amino acid of the N-terminal side fragment of the Cre protein and the N-terminal amino acid of the C-terminal fragment.

Described specifically, in the set of two polypeptides according to the present invention, the N-terminal side fragment and the C-terminal side fragment of the Cre protein having an amino acid sequence of SEQ ID NO: 1 bind to two proteins light-dependently forming a dimer, respectively. The term "bind" as used herein means that the N-terminal side fragment and the C-terminal side fragment of the Cre protein having an amino acid sequence of SEQ ID NO: 1 bind directly or via a linker to two proteins light-dependently forming a dimer, respectively.

In other words, in the set of two polypeptides according to the present invention, one of the polypeptides which are two proteins light-dependently forming a dimer is placed, via or without a linker, next to the C-terminal amino acid of the N-terminal side fragment of the Cre protein having an amino acid sequence of SEQ ID NO: 1 and the other one of the polypeptides which are two proteins light-dependently forming a dimer is placed, via or without a linker, next to the N-terminal amino acid of the C-terminal side fragment of the Cre protein having an amino acid sequence of SEQ ID NO: 1.

In the present invention, it is preferred that when the N-terminal side fragment of the Cre protein binds to, at the C-terminal amino acid thereof, pMag, pMagHigh1, pMagFast1, or pMagFast2 via a linker or without a linker, the C-terminal side fragment of the Cre protein binds to, at the N-terminal amino acid thereof, nMag, nMagHigh1, nMagFast1, or nMagFast2 via a linker or without a linker; or when the N-terminal side fragment of the Cre protein binds to, at the C-terminal amino acid thereof, nMag, nMagHigh1, nMagFast1, or nMagFast2 via a linker or without a linker, the C-terminal side fragment of the Cre protein binds to, at the N-terminal amino acid thereof, pMag, pMagHigh1, pMagFast1, or pMagFast2 via a linker or without a linker.

In the set of two polypeptides according to the present invention, it is more preferred that the N-terminal side fragment of the Cre protein binds to, at the C-terminal amino acid thereof, nMag, nMagHigh1, nMagFast1, or nMagFast2 via a linker and the C-terminal side fragment of the Cre protein binds to, at the N-terminal amino acid thereof, pMag, pMagHigh1, pMagFast1, or pMagFast2 via a linker.

(Linker)

In the present invention, not only the linker for binding the N-terminal side fragment or the C-terminal side fragment of the Cre protein to two proteins light-dependently forming a dimer, but also, when two respective domains constituting two polypeptides of the polypeptide set of the present invention bind to each other, a linker for binding these domains to each other may be interposed.

A known linker can be used as the linker to be used in the invention without particular limitation and a linker having an amino acid sequence abundantly containing therein glycine and serine is used. It is the common practice to use a linker having glycine as a main component and a linker containing serine or threonine, which is a hydrophilic amino acid, is preferred.

In the present invention, when two domains are bound to each other via a linker, they can be bound by making use of a restriction enzyme recognition site as its gene engineering method. The restriction enzyme recognition site is mostly made of six base sequences, so that when two domains are bound to each other by making use of a restriction enzyme recognition site, two amino acids are introduced between these domains.

Such a restriction enzyme recognition site can also be used as a linker in the present invention.

No particular limitation is imposed on the linker in the present invention and it may be made of from 2 to 16 amino acids.

In the present invention, examples of the domain include the N-terminal side fragment and the C-terminal side fragment of the Cre protein constituting the set of two polypeptides according to the present invention and two proteins light-dependently forming a dimer. Additional examples of the domain include a nuclear localization signal sequence and a 2A peptide sequence.

(Nuclear Localization Signal Sequence)

The set of two polypeptides according to the present invention may have a nuclear localization signal sequence.

When the set has a nuclear localization signal sequence, it may bind to the C-terminal amino acid of one of the polypeptides, which are two proteins light-dependently forming a dimer, to be bound to the C-terminal amino acid of the N-terminal side fragment of the Cre protein via a linker or without a linker; or it may bind to the N-terminal amino acid of the other one of the polypeptides, which are two proteins light-dependently forming a dimer, to be bound to the N-terminal amino acid of the C-terminal side fragment of the Cre protein via a linker or without a linker.

The nuclear localization signal sequence may be present in one of the two polypeptides constituting the polypeptide set of the present invention or may be present in the two polypeptides.

The nuclear localization signal sequence is not particularly limited and examples of it include an amino acid sequence VPKKKRKV (SEQ ID NO: 23) and KRTADGSEFESPKKKRKVEAS (SEQ ID NO: 24).

(2A Peptide Sequence)

The set of two polypeptides according to the present invention is expressed preferably by using a polypeptide called "2A peptide" which is cleaved autocatalytically and capable of adjusting a ratio of the amounts of the proteins on both sides of the 2A peptide to be bound thereto respectively via the N-terminal amino acid and the C-terminal amino acid to 1:1.

The set of two polypeptides according to the present invention therefore preferably has amino acid sequences (2A peptide sequences) derived from the autocatalytically cleaved 2A peptide. The term "the set of two polypeptides according to the present invention has 2A peptide sequences" means that two polypeptides constituting the polypeptide set each have a partial sequence of the 2A peptide to be cleaved cotranslationally.

The 2A peptide is not particularly limited and examples include peptides described in Kim, J. H., et al., PLoS One. 6(4), e18556 (2011). For example, polypeptides such as P2A peptide, T2A peptide, E2A peptide, and F2A peptide are known.

Figure 3:
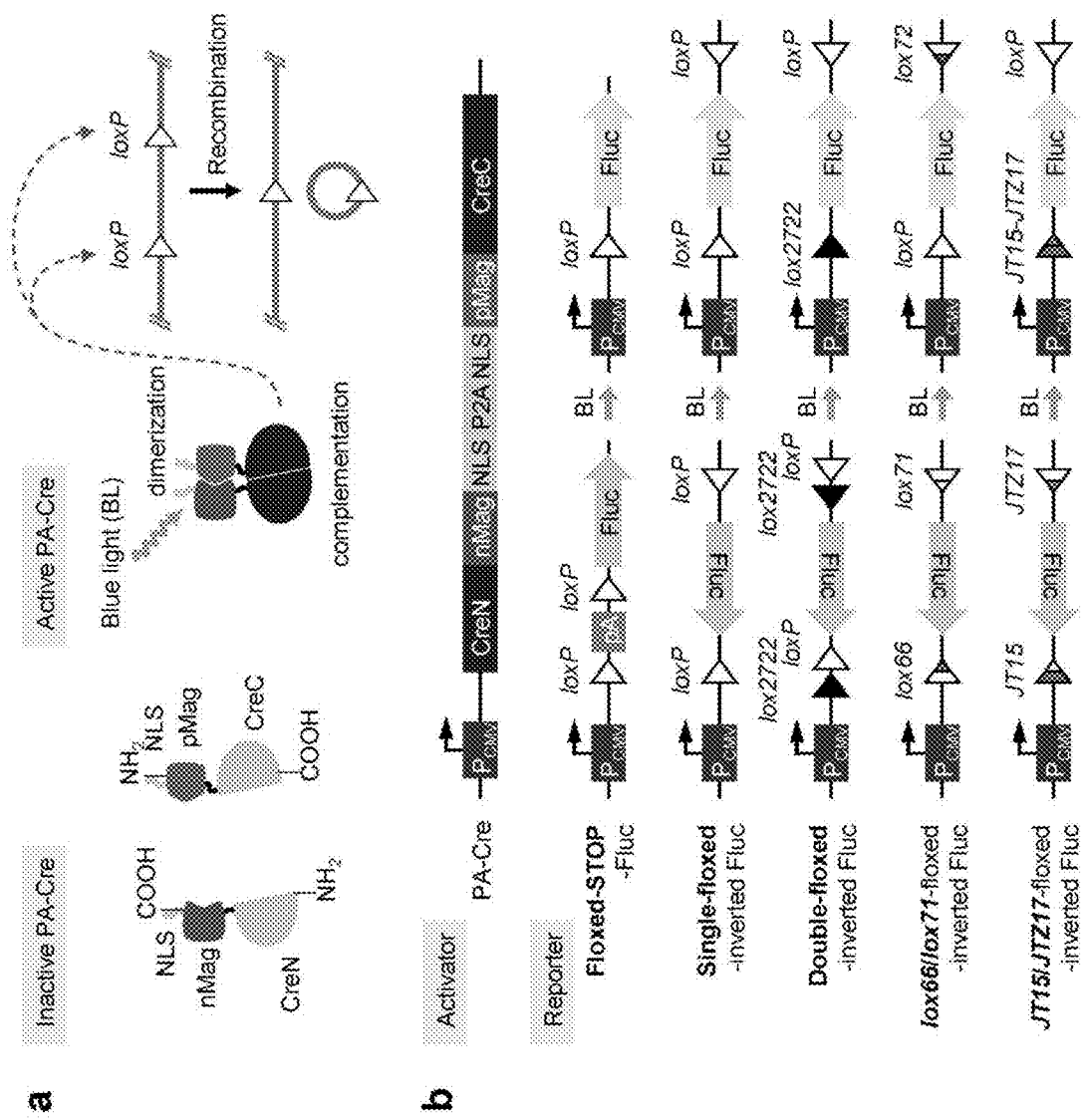
FIG. 3 shows a conceptual diagram of optogenetics of a DNA recombination reaction by PA-Cre. (a) shows the principal of DNA recombination by PA-Cre. PA-Cre has no activity in a dark place (Inactivate PA-Cre), but it is activated by illumination with a light (Activate PA-Cre) and catalyzes DNA recombination between two loxP sequences. (b) shows one example of an expression vector of PA-Cre and an example of a reporter for evaluating the DNA recombination by PA-Cre. The lox2722, lox66, lox71, JT15, and JTZ17 are each a mutant of loxP. PA-Cre can catalyze the DNA recombination of any of these mutants as it catalyzes that of the loxP. P2A represents a 2A peptide sequence, PCMV represents a CMV promoter, pA represents a stop-transfer sequence, and Fluc represents the cDNA of luciferase.

The set of two polypeptides according to the present invention is preferably a set of two polypeptides expressed as an amino acid sequence having respective domains placed therein and obtained by autocatalytic cleavage of a P2A peptide as shown in FIG. 3b. This will be described with a P2A peptide sequence as an example. GSGATNFSLLKQAGDVEENPGP (SEQ NO: 6) which is a P2A peptide sequence is cleaved cotranslationally between the sequence GP of the C-terminal thereof and "GSGATNFSLLKQAGDVEENPG" remains for a polypeptide to be bound to the N-terminal amino acid of the P2A peptide sequence, while "P" remains for a polypeptide to be bound to the C-terminal amino acid of the P2A peptide sequence.

It is preferred that as the set of two polypeptides according to the present invention, one of the two polypeptides constituting the set has, from the N-terminal side to the C-terminal side thereof, the following amino acid sequences in order of mention: the N-terminal side fragment of the Cre protein, a protein light-dependently forming a dimer, a nuclear localization signal sequence, and a portion of a 2A peptide sequence, while the other polypeptide has, from the N-terminal side to the C-terminal side, the following amino acid sequences in order of mention: a portion of a 2A peptide sequence, a nuclear localization signal sequence, a protein light-dependently forming a dimer, and the C-terminal side fragment of the Cre protein.

The "N-terminal side fragment of the Cre protein", "C-terminal side fragment of the Cre protein", "protein light-dependently forming a dimer", "nuclear localization signal sequence", and "2A peptide sequence", each recognized as a domain in the present specification, may be arranged in the polypeptide in order of mention and these domains may have therebetween an amino acid sequence serving as a linker.

In the set of two polypeptides according to the present invention, the domains are placed from the N terminal to the C terminal. Binding between domains, more specifically, binding between the N-terminal side fragment of the Cre protein and the protein light-dependently forming a dimer, binding between the protein light-dependently forming a dimer and the nuclear localization signal sequence, binding between the nuclear localization signal sequence and the portion of the 2A peptide sequence, binding between the portion of the 2A peptide sequence and the nuclear localization signal sequence, binding between the nuclear localization signal sequence and the protein light-dependently forming a dimer, and binding between the protein light-dependently forming a dimer and the C-terminal side fragment of the Cre protein may be binding via a linker.

The set of two polypeptides according to the present invention is preferably a set of a polypeptide having an amino acid sequence of SEQ ID NO: 25 and a polypeptide having an amino acid sequence of SEQ ID NO: 26 or a set of a polypeptide having an amino acid sequence of SEQ ID NO: 27 and a polypeptide having an amino acid sequence of SEQ ID NO: 28. These amino acid sequences are shown in FIGS. 14 and 15. It is to be noted that in each of the amino acid sequences, the underlined "MA" sequence means a sequence derived from an initiator codon and a Kozak sequence and the other underlined amino acid sequence means an amino acid sequence of a linker between domains.

(Nucleic Acid)

The present invention also provides a nucleic acid encoding two polypeptides constituting the polypeptide set.

The term "nucleic acid" as used herein includes DNA, RNA, and DNA/RNA chimera, and artificial nucleic acids such as locked nucleic acid (LNA) and peptide nucleic acid (PNA) unless otherwise particularly specified.

Examples of such nucleic acids include a nucleic acid encoding a fusion polypeptide between one of the polypeptides of the magnet and the N-terminal side fragment of the Cre protein and a nucleic acid encoding a fusion polypeptide between the other polypeptide of the magnet and the C-terminal side fragment of the Cre protein. A nucleic acid encoding both a fusion polypeptide between either one of the polypeptides of the magnet and the N-terminal side fragment or C-terminal side fragment of the Cre protein and a linker therebetween may also be used.

The nucleic acid according to the present invention may be a nucleic acid encoding also the nuclear localization signal sequence and the 2A peptide sequence or a nucleic acid encoding a polypeptide having a linker between domains thereof.

The nucleic acid according to the present invention may be a nucleic acid encoding a polypeptide having the following amino acid sequences in order of mention: the N-terminal side fragment of the Cre protein, a protein light-dependently forming a dimer, a nuclear localization signal sequence, a 2A peptide sequence, a nuclear localization signal sequence, a protein light-dependently forming a dimer, and the C-terminal side fragment of the Cre protein. The nucleic acid may also encode a polypeptide having, between domains thereof, an amino acid sequence serving as a linker. Examples of the base sequence of the nucleic acid are shown as SEQ ID NOS: 29 and 30 (FIGS. 16 and 17).

The nucleic acid according to the present invention can be synthesized based on a method known to those skilled in the art.

The present invention also embraces an expression vector including the nucleic acid of the present invention. The expression vector according to the present invention may have, inserted therein, either one of the nucleic acids respectively encoding the two polypeptides of the polypeptide set of the present invention; or may have, inserted therein, both the nucleic acids respectively encoding the two polypeptides of the set of the present invention. Examples of the nucleic acid inserted into the vector include respective base sequences of SEQ ID NOS: 29 and 30.

The nucleic acid of the present invention can be inserted into the downstream of a promoter of the expression vector as it is or after digestion with a restriction enzyme or addition of a linker. Examples of the vector include, but not limited to, *Escherichia coli*-derived plasmids (pBR322, pBR325, pUC12, pUC13, pUC18, pUC19, pUC118, pBluescript II, etc.), *Bacillus subtilis*-derived plasmids (pUB110, pTP5, pC1912, pTP4, pE194, pC194, etc.), yeast-derived plasmids (pSH19, pSH15, YEp, YRp, YIp, YAC, etc.), bacteriophages (λ phage, M13 phage, etc.), viruses (retrovirus, vaccinia virus, adenovirus, adeno-associated virus (AAV), cauliflower mosaic virus, tobacco mosaic virus, baculovirus, etc.), and cosmids.

The promoter can be selected as needed, depending on the kind of a host. When the host is an animal cell, for example, a SV40 (simian virus 40)-derived promoter or a CMV (cytomegalovirus)-derived promoter can be used. When the host is *Escherichia coli*, a trp promoter, a T7 promoter, a lac promoter, or the like can be used.

The expression vector may have therein a DNA replication origin (ori), a selection marker (antibiotic resistance, auxotrophy, etc.), an enhancer, a splicing signal, a poly A addition signal, a nucleic acid encoding a tag (FLAG, HA, GST, GFP, etc.), or the like.

A transformant can be obtained by transformation of an appropriate host cell with the expression vector of the present invention. The host can be selected as needed based on the relation with the vector and for example, *Escherichia coli, Bacillus subtilis*, bacteria of genus *Bacillus*), yeast, insects, inset cells, animal cells, and the like can be used. As the animal cells, for example, HEK293T cells, CHO cells, COS cells, myeloma cells, HeLa cells, and Vero cells may be used. Transformation can be performed by a known method such as lipofection, a calcium phosphate method, electroporation, microinjection, or particle gun, depending on the kind of the host.

By culturing the transformant by a conventional method, an intended polypeptide is expressed.

Purification of a protein from the cultured product of the transformant can be achieved by collecting cultured cells, suspending them in an appropriate buffer, destructing the cells by ultrasonic treatment, freezing and thawing, or the like method, and obtaining a crude extract by centrifugation or filtration. When the polypeptide is secreted in the culture medium, a supernatant is collected.

Purification from the crude extract or the culture supernatant can also be performed by a known method or a method based thereon (for example, salting-out, dialysis, ultrafiltration, gel filtration, SDS-PAGE, ion exchange chromatography, affinity chromatography, or reverse-phase high-performance liquid chromatography).

The present invention also provides a Cre-loxP system for use in novel light-dependent genetic recombination by using the set of two polypeptides according to the present invention in combination with a nucleic acid having a loxP sequence or a loxP mutant sequence.

In the present invention, genetic recombination can be carried out in a manner similar to the Cre-loxP system except the Cre protein is split into an N-terminal side fragment and a C-terminal side fragment.

The Cre-loxP system according to the present invention may be a system using the nucleic acid of the present invention in combination with a nucleic acid having a loxP sequence or a loxP mutant sequence and the nucleic acid of the present invention is preferably a nucleic acid encoding the set of two polypeptides according to the present invention. The Cre-loxP system according to the present invention may be a Cre-loxP system having the expression vector of the present invention and a nucleic acid having a loxP sequence or a loxP mutant sequence.

As the loxP mutant, a nucleic acid having a sequence selected from the group consisting of lox2722, lox66, lox71, JT15, and JTZ17 may be used.

The present invention also provides an animal having the set of two polypeptides according to the present invention. In the animal, the set of two polypeptides according to the present invention may be present as a combination of two proteins as an N-terminal side fragment and a C-terminal side fragment; may be present as a nucleic acid encoding two polypeptides constituting the polypeptide set; or may be present as an expression vector.

The animal of the present invention may have the nucleic acid of the present invention; may have the nucleic acid of the present invention as an expression vector; or may have the Cre-loxP system of the present invention.

Since the set of two polypeptides according to the present invention has genetic recombination activity unexpectedly superior to that of a conventional light-dependently controlled split Cre, it can efficiently control genetic recombination even by illuminating an animal having, incorporated in the body thereof, the set of two polypeptides according to the present invention with a light from the outside of its body.

In short, the set of two polypeptides according to the present invention makes it possible to precisely control genetic recombination by a Cre/loxP system not only in vitro but also in vivo by switching ON/OFF the illumination with a light.

The animal having the Cre/loxP system of the present invention incorporated therein is not particularly limited insofar as it is a mammal and it is preferably a rodent as an experimental animal.

Although not particularly limited, use of an animal having the Cre/loxP system of the present invention incorporated therein makes it possible to knock out the activity of a gene by light stimulation or, on the contrary, return a mutant type gene to a normal one by light stimulation and thereby evaluate the influence of the gene; or to activate a reporter gene such as fluorescent protein by light stimulation and thereby label the biological tissue or cells constituting it.

Examples

The present invention will hereinafter be described specifically based on Examples, but the present invention is not limited to or by them. Those skilled in the art can modify the present invention into various aspects without departing from the significance of the present invention and such a modification is also embraced within the scope of the present invention.

Formation of PA-Cre Construct

Figure 2:
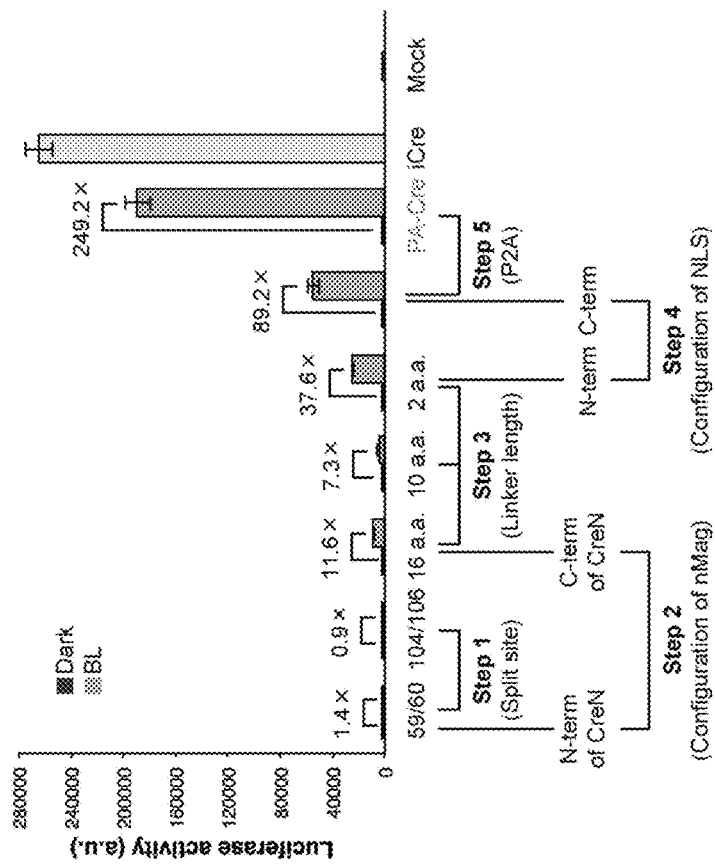
FIG. 2 shows evaluation results of luciferase assay of each of the constructs of PA-Cre shown in FIG. 1. (Step 1) shows the results when the Cre protein is cleaved between the 59th amino acid and the 60th amino acid (59/60) and between the 104th amino acid and the 106th amino acid (104/106). The (59/60) shows the results using CreN59 and CreC60 and the (104/106) shows the results when as split Cre, the N-terminal side fragment having a region of the amino acid sequence of SEQ ID NO: 1 between position 19 and position 104 and the C-terminal side fragment having a region of the amino acid sequence of SEQ ID NO: 1 between position 106 and position 343 are used. (Step 2) shows the results of a construct in which nMag is bound to the N-terminal amino acid of CreN59 and a construct in which nMag is bound to the C-terminal amino acid of CreN59. (Step 3) shows, in a construct in which nMag is bound to the C terminal amino acid of CreN59 via a linker and a construct in which CreC60 is bound to the C-terminal amino acid of pMag via a linker, the results of these constructs using, as a linker, three peptides different in length (16 a.a., 19 a.a., and 2 a.a.). (Step 4) shows the results of a construct in which a nuclear localization sequence (NLS) is bound to the N-terminal amino acid of CreN59 and a construct in which a nuclear localization sequence is bound to the C-terminal amino acid of nMag. (Step 5) shows the results of a construct having a P2A peptide sequence.

Various constructs formed as PA-Cre after investigation of a split site of Cre (Step 1), a binding position of magnet (pMag and nMag) to an N-terminal side fragment (CreN) and a C-terminal side fragment (CreC) of split Cre (Step 2), a linker length (Step 3), a binding position of a nuclear localization signal sequence (NLS) (Step 4), binding of a P2A peptide sequence (Step 5), and the like were evaluated by luciferase assay (FIGS. 1 and 2). For that purpose, COS-7 cells were seeded on a 96-well microplate (Corning, Corning, NY, USA) at a cell density of $1.5 \times 10^4$ cells/well and cultured for 24 hours under the conditions of 37° C. and 5% $CO_2$. Then, a cDNA encoding each of various PA-Cre constructs and a luciferase reporter plasmid were transfected at a ratio of 1:9 into the resulting cells at 37° C. A total amount of DNA used for the transfection was set at 0.05 μg/well. An X-tremeGENE 9 reagent was used for the transfection. From 24 hours after the transfection, the cells were illuminated with a blue light ($1.0$ W m$^{-2}$) for 24 hours. Immediately before the luciferase assay, the medium was replaced with a Hanks' balanced salt solution (HBSS, Grand Island Biological, Grand Island, NY, USA) containing 0.2 mM D-luciferin potassium salt (Wako, Japan). Bioluminescence was measured at room temperature for 10 seconds with a Centro XS$^3$ LB 960 plate reader (Berthold Technologies, Bad Wildbad, Germany) (FIG. 2).

Preparation of Plasmid

In order to form a PA-Cre construct, cDNAs encoding the N-terminal side fragment (CreN) and the C-terminal side fragment (Crec) of split Cre were prepared from the cDNA of an improved version (iCre) of Cre. The cDNA of iCre was synthesized using Invitrogen (Carlsbad, CA, UAS) to optimize a codon to enhance the expression of it in mammal cells. More specifically, ATGGCC (encoding MA, SEQ ID NO: 31) was added to materialize an initiator codon and a Kozak sequence.

For the preparation of the construct of CRY2-CIB1-splitCre, a plasmid (#26888) of CRY2-CreN$_{19-104}$ and a plasmid (#26889) of CIB1-CreC$_{106-343}$ were obtained from Addgene. Respective cDNAs encoding CreN$_{19-59}$, CreC$_{60-343}$, CreN$_{19-104}$, CreC$_{106-343}$, a Magnet system (pMag and nMag), and a nuclear localization signal sequence (NLS) were prepared by common PCR, restriction enzyme treatment, or ligation.

The construct of PA-Cre and the construct related thereto were each introduced into a pcDNA3.1 vector (Invitrogen) having a CMV promoter. The construct of PA-Cre-Y324F was prepared as a negative control by using Multi Site-Directed Mutagenesis (MBL) and substituting a 324th tyrosine residue with phenylalanine in accordance with the manual of the kit. CRY2-CIB1-splitCre was introduced into a pcDNA3.1 vector.

The construct of Floxed-STOP-Fluc was prepared by sandwiching a polyadenylation sequence (pA), a stop-transfer sequence, with two loxP sequences arranged in the same direction. On the other hand, the respective constructs of single-floxed-inverted Fluc, double-floxed-inverted Fluc, lox66/lox71-floxed inverted Fluc, and JT15/JTZ17-floxed inverted Fluc were prepared by reversing two or four loxP sequences or loxP mutant sequences and sandwiching the cDNA of firefly luciferase (Fluc) therebetween. The construct of Floxed-STOP-Fluc was prepared using a plasmid (#22797) obtained from Addgene. The cDNA of Fluc was obtained from a pGL4.31 vector (Promega). The respective constructs of Floxed-STOP-Fluc, single-floxed-inverted Fluc, double-floxed-inverted Fluc, lox66/lox71-floxed inverted Fluc, and JT15/JTZ17-floxed inverted Fluc were introduced into the pcDNA3.1 vector. Reporters using mCherry, a fluorescent protein, were prepared by substituting the cDNA of Fluc of the reporters using the above-described Fluc (floxed-STOP-Fluc, single-floxed-inverted Fluc, double-floxed-inverted Fluc, lox66/lox71-floxed inverted Fluc, and JT15/JTZ17-floxed inverted Fluc) with the cDNA of mCherry.

Cell Culturing

COS-7 cells, HEK-293 cells, NIH/3T3 cells, and HeLa cells (each, ATCC) were each cultured under the conditions of 37° C. and 5% $CO_2$ by using a Dulbecco's Modified Eagle Medium (DMEM, Sigma Aldrich) containing 10% FBS (GIBCO, Carlsbad, CA, USA), 100 unit/mL penicillin, and 100 μg/mL streptomycin (GIBCO). CHO-K1 cells (ATCC) were cultured under the conditions of 37° C. and 5% $CO_2$ by using a Ham's F-12 medium (GIBCO) containing 10% FBS, 100 unit/mL penicillin, and 100 μg/mL streptomycin.

Light Source

Figure 13:
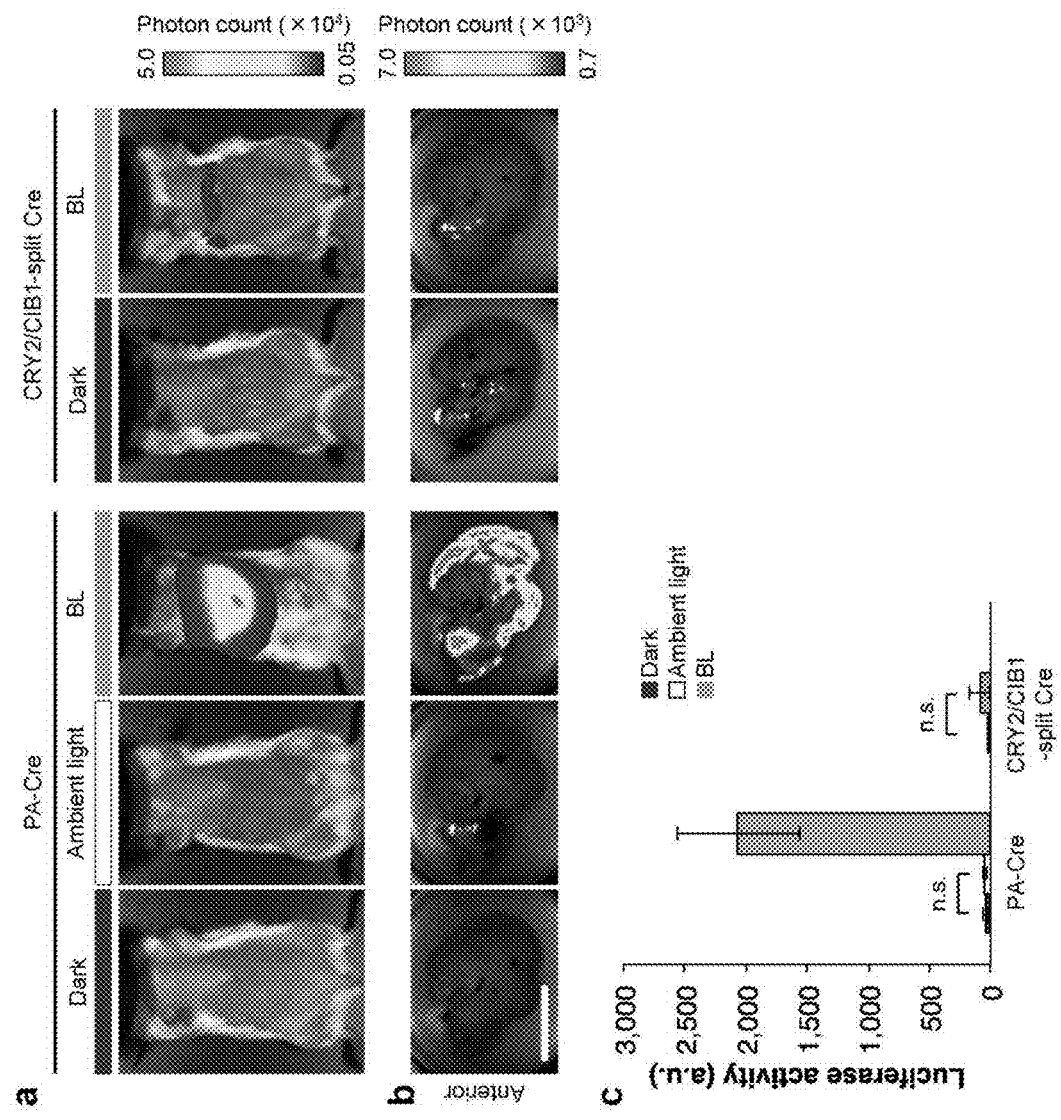
FIG. 13 shows the application results of PA-Cre to mice. (a) shows the comparison results when DNA recombination was optogenetically controlled at the liver of the mice by using PA-Cre and CRY2-CIB1-split Cre. Evaluation was made using a reporter (Floxed-STOP-Fluc of FIG. 3b) expressing luciferase by DNA recombination. PA-Cre can induce the expression of luciferase efficiently by illumination with light (16 hours) from the outside of the living body, but expression of luciferase is very weak when CRY2-CIB1-split Cre is used. In addition, PA-Cre does not induce expression of luciferase at the ambient light. (b) is an imaging view of light emission of luciferase when a mouse was illuminated with a light from the outside of its living body and then the liver was excised therefrom. PA-Cre can induce expression of luciferase efficiently, but almost no expression is observed when CRY2-CIB1-split Cre is used. PA-Cre does not induce expression of luciferase at the ambient light. (c) collectively shows the results obtained by repeating the investigation of FIG. 13b.

A LED light source (470±20 nm; CCS, Kyoto, Japan) was used for illuminating cells or mice expressing PA-Cre with a light (FIGS. 6 to 10, 12, and 13). A white fluorescent lamp was used to study the response of PA-Cre to ambient light (FIG. 13).

Evaluation of PA-Cre

Figure 6:
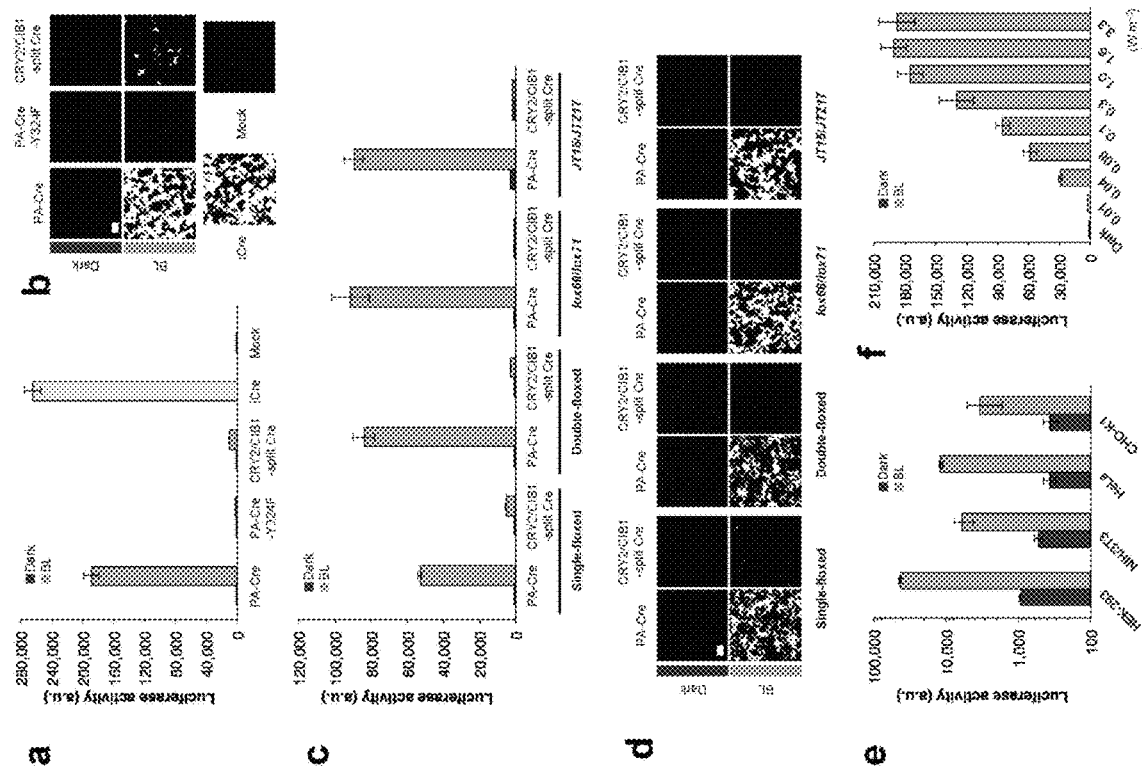
FIG. 6 shows the evaluation results of PA-Cre. (a) shows that the DNA recombination activity of PA-Cre is induced by illumination with a light. Evaluation was made using a reporter (Floxed-STOP-Fluc of FIG. 3b) which expresses luciferase by DNA recombination. Shown are PA-Cre-Y324F: a mutant from which DNA recombination activity has been deleted, CRY2-CIB1-split Cre: a light-dependent DNA recombination system using split Cre and photo-switchable protein CRY2-CIB1 (refer to Non-Patent Document 2), and iCre: a protein obtained by linking a nuclear localization signal sequence to a full-length Cre protein and iCre as a control. (b) shows the results of a test performed by replacing the luciferase reporter used in FIG. 6a with a reporter (Floxed-STOP-mCherry) which expresses mCherry, a fluorescent protein, by DNA recombination. Similar to FIG. 6a, this shows that DNA recombination activity of PA-Cre can be optically controlled. (c) For comparison of the response to various loxP mutants between PA-Cre and CRY2-CIB1-split Cre, evaluation was made using a reporter disclosed in FIG. 3b and expressing luciferase by DNA recombination. PA-Cre efficiently causes a DNA recombination reaction of any of the loxP mutants, while CRY2-CIB1-split Cre has a low DNA recombination efficiency. In particular, CRY2-CIB1-split Cre shows a markedly low DNA recombination efficiency to a reporter using lox66, lox71, JT15, or JTZ17. (d) shows the results of a test made after substituting a series of luciferase reporters used in FIG. 6c with a reporter expressing mCherry, a fluorescent protein, by DNA recombination. Similar to FIG. 6c, PA-Cre efficiently causes a DNA recombination reaction of any loxP mutant, while CRY2-CIB1-split Cre has a low DNA recombination efficiency. (e) shows the evaluation results of PA-Cre in various cell species. (f) shows the results of the DNA recombination activity of PA-Cre dependent on light illumination intensity.
Figure 9:
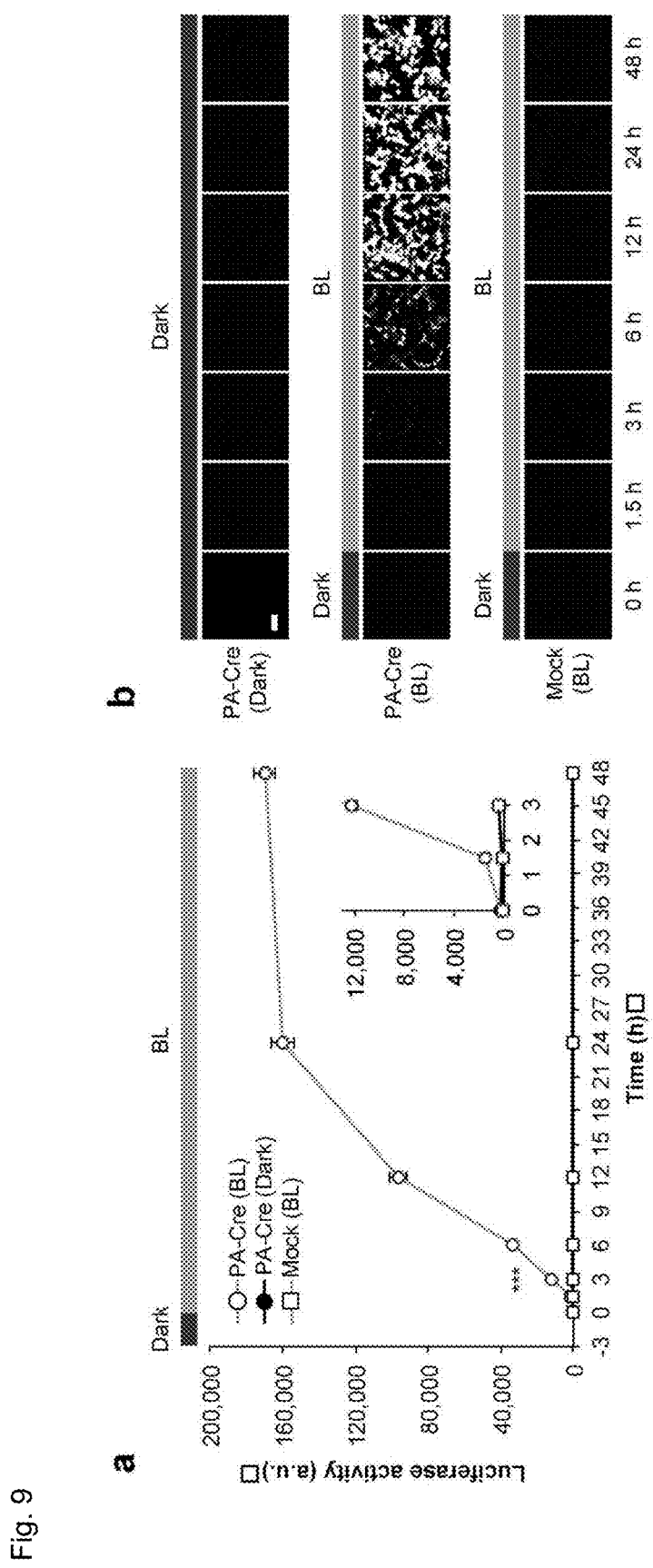
FIG. 9 shows the kinetics of a DNA recombination reaction of PA-Cre. (a) shows the results of applying light illumination to cells expressing PA-Cre for varied times and evaluating the kinetics of a DNA recombination reaction by PA-Cre. Evaluation was made using a reporter expressing luciferase by DNA recombination (Floxed-STOP-Fluc of FIG. 3b) (b) shows the evaluation results of the kinetics of a DNA recombination reaction by PA-Cre by using a reporter which expresses mCherry, a fluorescent protein, by DNA recombination (Floxed-STOP-mCherry).
Figure 10:
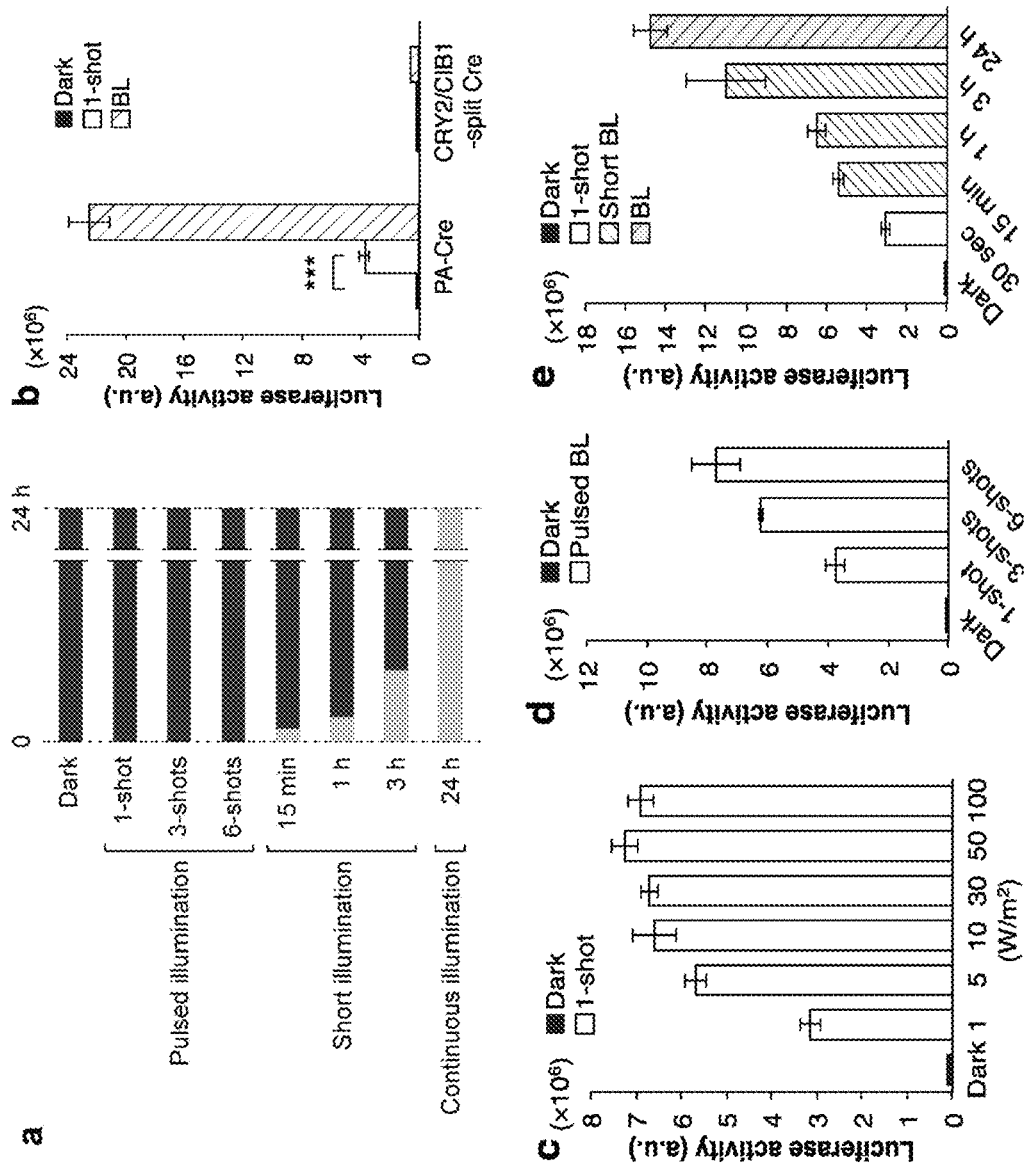
FIG. 10 shows the investigation results of light illumination conditions in a DNA recombination reaction by PA-Cre. (a) shows an example of various light illumination conditions. (b) For comparison of the response to various light illumination conditions between PA-Cre and CRY2-CIB1-split Cre, evaluation was made using a reporter expressing luciferase by DNA recombination (Floxed-Stop-Fluc of FIG. 3b). PA-Cre can optogenetically control a DNA recombination reaction sufficiently not only in light illumination for long hours but also in light illumination (1-shot) for as short as about 30 seconds. (c) A DNA recombination reaction efficiency by PA-Cre was evaluated when light illumination (1-shot) for about as short as 30 seconds was performed at various light illumination intensities. (d) A DNA recombination reaction efficiency by PA-Cre was evaluated when light illumination for as short as about 30 seconds was repeated. (e) A DNA recombination reaction efficiency by P-Cre was evaluated when a light illumination time was varied.
Figure 11:
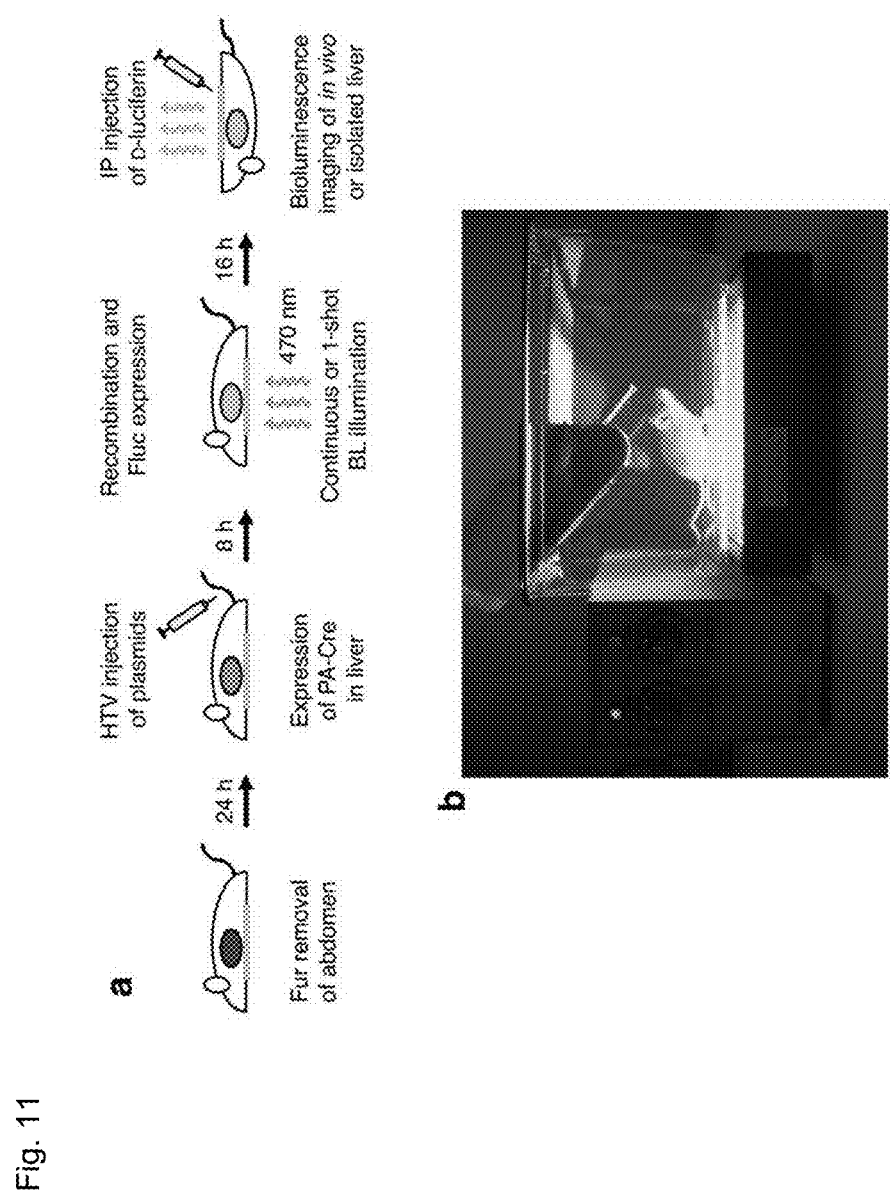
FIG. 11 shows a conceptual diagram of application of PA-Cre to a mouse. (a) shows the outline of a test procedure for optogenetically control, with PA-Cre, a DNA recombination reaction in the deep part of the living body of the mouse. (b) shows a non-invasive light illumination test from the outside of the living body by using a LED light source.
Figure 12:
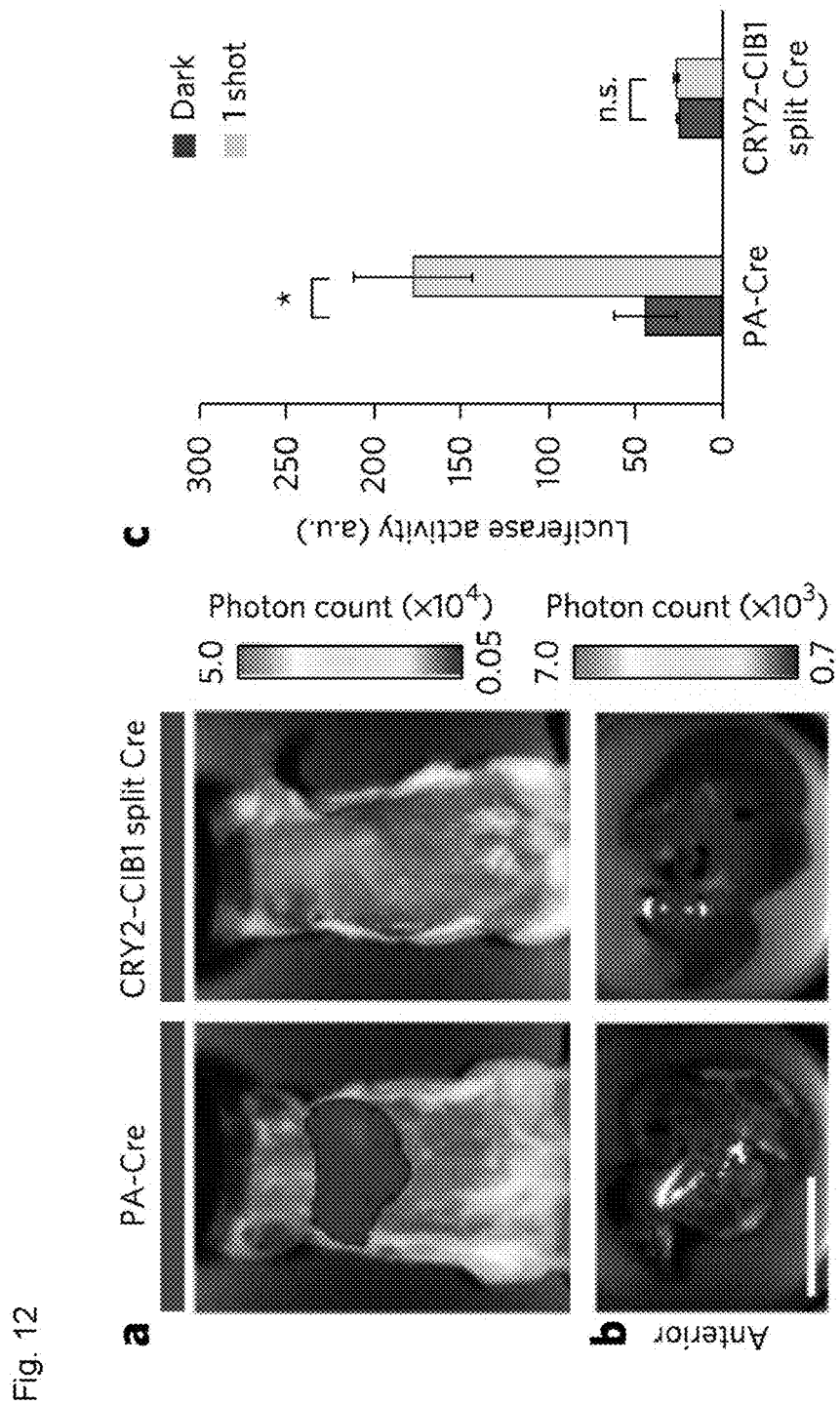
FIG. 12 shows the results of DNA recombination optogenetically controlled at the deep part of the living body of the mouse. (a) shows the comparison results when DNA recombination was optogenetically controlled at the liver of a mouse by using PA-Cre and CRY2-CIB1-split Cre. Evaluation was made using a reporter (Floxed-STOP-Fluc of FIG. 3b) which expresses luciferase by DNA recombination. PA-Cre can induce expression of luciferase efficiently even by illumination with light from the outside of the living body for as short as 30 seconds, while expression is not observed when CRY2-CIB1-split Cre is used. (b) shows an imaging view of light emission of luciferase when a mouse was illuminated with light for as short as 30 seconds from the outside of its living body and then the liver was excised from the mouse. PA-Cre can induce expression of luciferase efficiently, but expression is not observed when CRY2-CIB1-split Cre is used. (c) collectively shows the results obtained by repeating the investigation of FIG. 12b.

For luciferase assay, COS-7 cells were seeded in a 96-well microplate (Corning, Corning, NY, USA) at a cell density of $1.5 \times 10^4$ cells/well and cultured for 24 hours under the conditions of 37° C. and 5% $CO_2$ (FIGS. 6, 9, and 10). Then, a cDNA encoding PA-Cre (or CRYS2-CIB1-split Cre) and a luciferase reporter plasmid were transfected at a ratio of 1:9 into the resulting cells at 37° C. A total amount of DNA used for the transfection was set at 0.05 μg/well. An X-tremeGENE 9 reagent was used for the transfection. From 24 hours after the transfection, the cells were illuminated with a blue light ($1.0$ W m$^{-2}$) for 24 hours. Immediately before the luciferase assay, the medium was substituted with a Hanks' balanced salt solution (HBSS, Grand Island Biological, Grand Island, NY, USA) containing 0.2 mM D-luciferin potassium salt (Wako, Japan). Bioluminescence was measured at room temperature for 10 seconds with a Centro XS$^3$ LB 960 plate reader (Berthold Technologies, Bad Wildbad, Germany).

For a control test, COS-7 cells were seeded on a 96-well microplate at a cell density of $1.5 \times 10^4$ cells/well and cultured for 24 hours under the conditions of 37° C. and 5% $CO_2$ (FIG. 6). Then, a cDNA encoding PA-Cre-Y324F (iCre or pcDNA3.1 vector) and a luciferase reporter plasmid were transfected at a ratio of 1:9 into the resulting cells at 37° C. For the transfection, 0.05 μg/well of DNA was used and the transfection was carried out with an X-tremeGENE 9 reagent. From 24 hours after the transfection, the cells were illuminated with a blue light ($1.0$ W m$^{-2}$) for 24 hours and bioluminescence was measured. When the iCre was used, bioluminescence was measured after incubating the cells in a dark place for 48 hours from the transfection.

In order to study dependence of control of PA-Cre on the intensity of light illumination, a 96-well microplate was masked with an ND filter (Fujifilm, Tokyo, Japan) having a transmittance of 40%, 33%, 25%, or 10% (FIG. 6). COS-7 cells were seeded on the 96-well microplate at a cell density of $1.5 \times 10^4$ cells/well and cultured for 24 hours under the conditions of 37° C. and 5% $CO_2$. Then, a cDNA encoding PA-Cre and a Floxed-STOP-Fluc plasmid were transfected at a ratio of 1:9 into the resulting cells at 37° C. For the transfection, 0.05 µg/well of DNA was used and the transfection was carried out with an X-tremeGENE 9 reagent. From 24 hours after the transfection, the cells were illuminated with a blue light (1.0 W m$^{-2}$) for 24 hours and bioluminescence was measured.

In order to study the light response of PA-Cre in various cell species, HEK-293 cells, NIH/3T3 cells, and CHO-K1 cells were each seeded on a 96-well microplate at a cell density of 1.5×10$^4$ cells/well (FIG. 6). HeLa cells were seeded on a 96-well microplate at a cell density of 3.0×10$^4$ cells/well. Those cells were cultured for 24 hours under the conditions of 37° C. and 5% $CO_2$. Into the HEK-293 cells, a cDNA encoding PA-Cre and a Floxed-STOP-Fluc plasmid were transfected at a ratio of 1:9 at 37° C. For the transfection, 0.05 µg/well of DNA was used and the transfection was carried out with an X-tremeGENE 9 reagent. Into the NIH/3T3 cells, HeLa cells, and CHO-K1 cells, a cDNA encoding PA-Cre and a Floxed-STOP-Fluc plasmid were transfected at a ratio of 1:9 at 37° C. For the transfection, 0.3 µg/well of DNA was used and the transfection was carried out with a Lipofectamine 3000 reagent. From 24 hours after the transfection, the cells were illuminated with a blue light (1.0 W m$^{-2}$) for 24 hours and bioluminescence was measured.

For evaluation based on fluorescence imaging, COS-7 cells were seeded on a Lab-Tek 8-well chambered cover glasses (Thermo Scientific, Waltham, USA) at a cell density of 3.0×10$^4$ cells/well and cultured for 24 hours under the conditions of 37° C. and 5% $CO_2$ (FIGS. 6 and 9). Then, a cDNA encoding PA-Cre or CRY2-CIB1-split Cre and a reporter plasmid thereof were transfected at a ratio of 1:9 into the resulting cells at 37° C. For the transfection, 0.15 µg/well of DNA was used and the transfection was carried out with an X-tremeGENE 9 reagent. From 24 hours after the transfection, the cells were illuminated with a blue light (1.0 W m$^{-2}$) for 24 hours. The medium was replaced with HBSS immediately before fluorescence imaging. The fluorescence imaging was carried out with an LSM 710 confocal Laser-scanning microscope (CarlZeiss, Jena, Germany) loaded with a 63× oil objective. For fluorescence imaging of mCherry, HeNe laser (543 nm) was used.

Pattern Illumination

Figure 7:
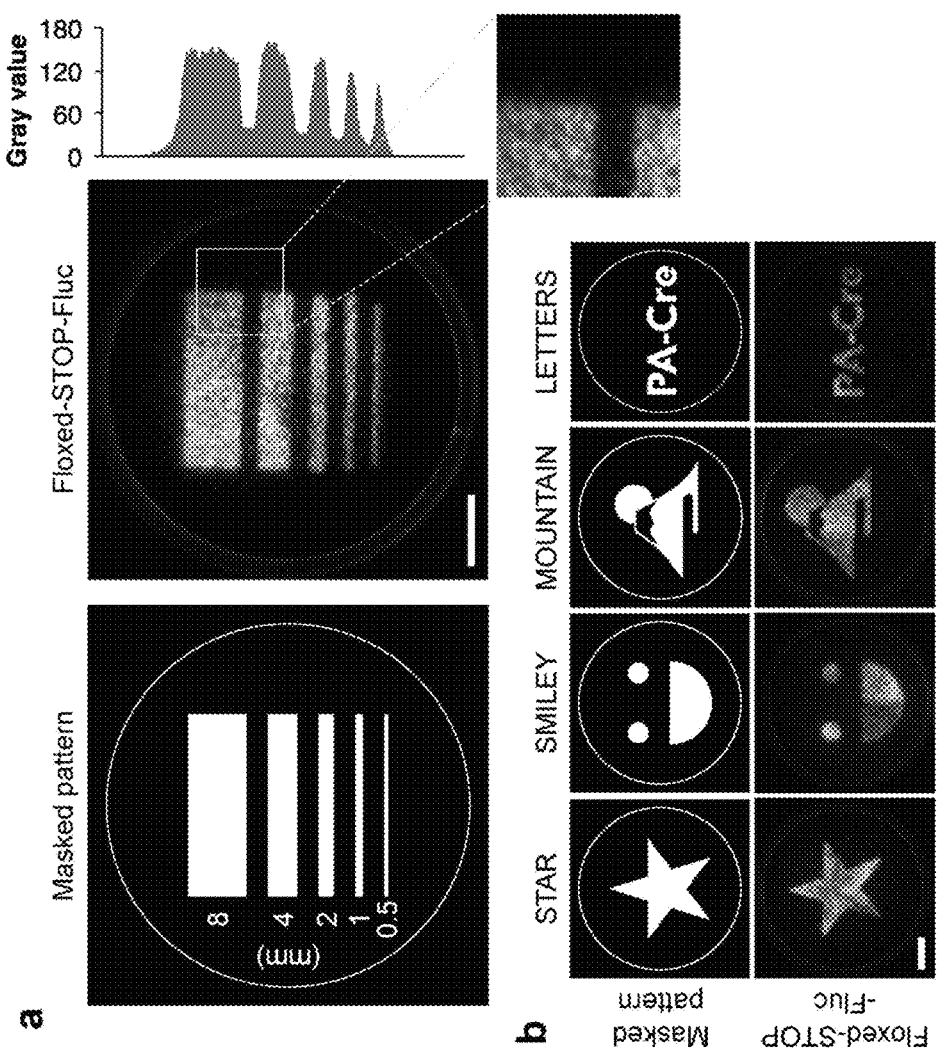
FIG. 7 shows the results of spatial control of a DNA recombination reaction by PA-Cre. (a) and (b) show the results of applying pattern illumination to cells cultured on a 6-cm dish and thereby effecting spatial control of a DNA recombination reaction. A reporter (Floxed-STOP-Fluc of FIG. 3b) expressing luciferase by DNA recombination is used.
Figure 8:
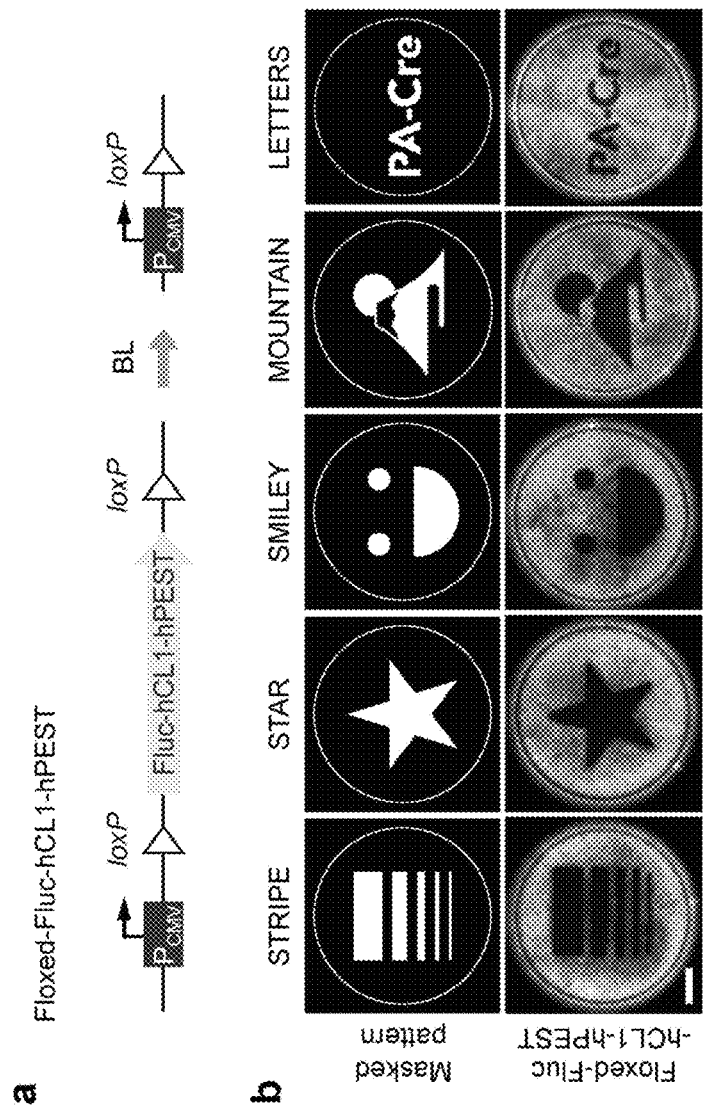
FIG. 8 shows the evaluation results of PA-Cre. (a) shows a conceptual diagram of the design of a reporter whose luciferase gene is knocked out by DNA recombination. (b) shows the results of applying pattern illumination to cells cultured on a 6-cm dish and thereby effecting spatial control of a DNA recombination reaction. The reporter of FIG. 8a whose luciferase gene is knocked out by DNA recombination is used.

COS-7 cells were seeded on a 6-cm culture dish (Thermo Scientific) at a cell density of 1.4×10$^6$ cells/dish and the cells were cultured for 24 hours under the conditions of 37° C. and 5% $CO_2$ (FIGS. 7 and 8). The culture dish was used after forming, on the bottom surface thereof, light masks having various patterns (STRIPE, STAR, SMILEY, MOUNTAIN, and LETTERS) with a black vinyl tape. A cDNA encoding PA-Cre and a Floxed-STOP-Fluc plasmid were transfected at a ratio of 1:9 at 37° C.; or a cDNA encoding PA-Cre and a Floxed-Fluc-hCL1-hPEST plasmid were transfected at 1:4 at 37° C. For the transfection, 2.5 µg/dish of DNA was used and the transfection was carried out with an X-tremeGENE 9 reagent. From 24 hours after the transfection, the cells were illuminated with a blue light (1.0 W m$^{-2}$) for 48 hours. Prior to bioluminescence imaging, the medium was replaced with HBSS containing 1 mM D-luciferin. The bioluminescence imaging was carried out for 5 minutes using a Lumazone bioluminescence imager (Nippon Roper, Tokyo, Japan) loaded with an Evolve 512 EMCCD camera (Photomerics). The data thus obtained were analyzed using a slidebook 4.2 software (Intelligent Innovations Inc., Denver, CO) and an Image-J software.

Measurement of Kinetics of DNA Recombination Reaction of PA-Cre

For luciferase assay, COS-7 cells were seeded on a 96-well microplate at a cell density of 1.5×10$^4$ cells/well and were cultured for 24 hours under the conditions of 37° C. and 5% $CO_2$ (FIG. 9). A cDNA encoding PA-Cre and a Floxed-STOP-Fluc plasmid were transfected at a ratio of 1:9 into the resulting cells at 37° C. For the transfection, 0.05 µg/well of DNA was used and the transfection was carried out with an X-tremeGENE9 reagent. From 24 hours after the transfection, the cells were illuminated with a blue light (1.0 W m$^{-2}$) for varied hours (0, 1.5, 3, 6, 12, 24, and 48 hours). The medium was replaced with HBSS containing 0.2 mM D-luciferin. Bioluminescence was measured at room temperature for 10 seconds with a Centro XS$^3$ LB 960 plate reader. For a control test, COS-7 cells were transfected with a pcDNA3.1 vector (Mock) and a Floxed-STOP-Fluc plasmid under the conditions similar to those described above and bioluminescence was measured.

In order to carry out fluorescence evaluation of a DNA recombination reaction with PA-Cre, COS-7 cells were seeded on an 8-well chambered coverglass at a cell density of 3.0×10$^4$ cells/well and cultured for 24 hours under the conditions of 37° C. and 5% $CO_2$ (FIG. 9). A cDNA encoding PA-Cre and a Floxed-STOP-mCherry plasmid were transfected at a ratio of 1:9 into the resulting cells at 37° C. For the transfection, 0.15 µg/well of DNA was used and the transfection was carried out with an X-tremeGENE9 reagent. From 24 hours after the transfection, the cells were illuminated with a blue light (1.0 W m$^{-2}$) for varied hours (0, 1.5, 3, 6, 12, 24, and 48 hours). Immediately before fluorescence imaging, the medium was replaced with HBSS. Fluorescence imaging was carried out with an LSM 710 confocal laser-scanning microscope (CarlZeiss, Jena, Germany) loaded with a 63× oil objective. For fluorescence imaging of mCherry, HeNe laser (543 nm) was used. For a control test, a pcDNA3.1 vector (Mock) and a Floxed-STOP-mCherry plasmid were transfected into COS-7 cells under the conditions similar to those described above and fluorescence imaging was carried out.

Investigation of Dependence on Light Illumination Time

COS-7 cells were seeded on a 35-mm culture dish (IWAKI, Tokyo, Japan) at a cell density of 2.0×10$^5$ cells/dish and cultured for 24 hours under the conditions of 37° C. and 5% $CO_2$ (FIG. 10). A cDNA encoding PA-Cre and a Floxed-STOP-Fluc plasmid were transfected at a ratio of 1:9 into the resulting cells at 37° C. For the transfection, 1.0 µg/dish of DNA was used and the transfection was carried out with an X-tremeGENE9 reagent. From 24 hours after the transfection, the cells were illuminated with a blue light for varied time patterns as follows. Bioluminescence was measured by illuminating the cells with a blue light of 50 W m$^{-2}$ for 30 seconds, followed by incubation for 24 hours in a dark place. Bioluminescence was also measured by illuminating the cells with a blue light of 50 W m$^{-2}$ for 30 seconds at three times or six times at an interval of 30 minutes, followed by incubation in a dark place. In a 1-shot illumination test, illumination with a blue light (50 W m$^{-2}$) for 15 minutes, 1 hour, or 3 hours was studied, in addition to illumination for 30 seconds. As a control test, illumination of the cells with a blue light (1.0 W m$^{-2}$) for 24 hours was also carried out. Prior to bioluminescence measurement, the medium was replaced with HBSS containing 0.2 mM D-luciferin. Bioluminescence was measured at room temperature for 1.0 second with a GloMax 96 microplate luminometer (Promega).

DNA Recombination Reaction in Mice

In a test, 5-week old female BALB/c mice (Sankyo Labo Service Corporation, Inc., Tokyo, Japan) were used (FIGS.

12 and 13). The mice were depilated at the abdominal zone thereof with a depilatory cream and then kept in a cage for 24 hours. Then, a cDNA encoding PA-Cre and a Floxed-STOP-Fluc plasmid used were injected at a ratio of 1:9 into the caudal vein of the mice at 37° C. The hydrodynamic injection was carried out with a TransIT-QR Hydrodynamic Delivery Solution (MirusBio LLC, Madison, WI, USA) in accordance with its manual. An amount of the DNA and a volume of the solution thus injected were 300 μg/mouse weight (g) and 0.1 mL/mouse weight (g), respectively. After the hydrodynamic injection, the mice were kept in a dark place for 8 hours and illuminated with a light from a blue LED light source (470±20 nm, 200 W m$^{-2}$) for 16 hours or 30 seconds in the cage. The mice illuminated with the light for 30 seconds were kept in a dark place for further 16 hours. In order to study illumination with an ambient light, the mice subjected to hydrodynamic injection were kept for 24 hours under white fluorescence (0.05 W m$^{-2}$). Bioluminescence imaging of the mice was carried out 24 hours after the hydrodynamic injection. Prior to the bioluminescence imaging, 100 mM D-luciferin was injected into the caudal vein of the mice. The D-luciferin solution was 10 μL/mouse weight (g). Three minutes after the injection of D-luciferin, bioluminescence imaging was carried out for 5 minutes by a Lumazone bioluminescence imager (Nippon Roper) loaded with an Evolve 512 EMCCD camera (Photometrics). Between injection of D-luciferin into the caudal vein and the bioluminescence imaging, the mice were anesthetized with isoflurane (Abbvie, Tokyo, Japan) to suppress their movement. In order to ex vivo analysis after in vivo bioluminescence imaging of mice, the liver was excised from the mice. The liver was put in PBS containing 1 mM D-luciferin. For the test, a 6-well culture plate (Thermo Scientific) was used. The respective images of the anterior and posterior parts of the excised liver were taken using a Lumazone biolumines-cence imager (Nippon Roper) for 5 minutes. The data were analyzed by a slidebook 4.2 software (Intelligent Innovations Inc.).

SEQUENCE LISTING FREE TEXT

SEQ ID NO: 1 represents the amino acid sequence of the Cre protein.
SEQ ID NO: 2 represents the amino acid sequence of the Vivid protein.
SEQ ID NOS. 3 to 5 represent the respective amino acid sequences of the linkers.
SEQ ID NO: 6 represents the amino acid sequence (P2A peptide sequence) of the P2A peptide.
SEQ ID NOS: 7 to 12 represent the respective base sequences of the loxP and loxP mutants (lox2722, lox66, lox71, JT15, and JTZ17).
SEQ ID NOS: 13 and 14 represent the respective base sequences of lox72 and JA15-JTZ17, which are products of DNA recombination.
SEQ ID NOS: 15 to 22 represent the respective amino acid sequences of pMag, pMagHigh1, pMagFast1, pMagFast2, nMag, nMagHigh1, nMagFast1, and nMagFast2.
SEQ ID NOS: 23 and 24 represent the respective amino acid sequences of nuclear localization signal sequences given as examples.
SEQ ID NOS: 25 to 28 represent the respective amino acid sequences of two polypeptides constituting the polypeptide set (PA-Cre) according to the present invention.
SEQ ID NOS: 29 and 30 represent the respective base sequences to be inserted into the vector of the set (PA-Cre) of two polypeptides according to the present invention.
SEQ ID NO: 31 represents the base sequence encoding the MA amino acid sequence for the initiator codon of PA-Cre and the Kozak sequence.

What is claimed is:

1. A set of two polypeptides, which comprises
a first polypeptide comprising an N-terminal side fragment of a Cre protein, said Cre protein having the amino acid sequence SEQ ID NO: 1 and a second polypeptide comprising a C-terminal side fragment of the Cre protein, wherein:
the N-terminal side fragment and the C-terminal side fragment are cleavage products resulting from cleavage between amino acid positions 59 and 68 or 101 and 111 of SEQ ID NO: 1;
the N-terminal side fragment is linked, at its C-terminal amino acid, to a first protein;
the C-terminal side fragment is linked, at its N-terminal amino acid, to a second protein;
said first and second proteins light-dependently form a dimer; and
the first and second proteins each independently comprise a polypeptide comprising the amino acid sequence of SEQ ID NO: 2 or a variant of the amino acid sequence of SEQ ID NO: 2 with amino acid substitutions at positions 52 and 55; positions 52, 55, and 85; positions 52, 55, 74, and 85; or positions 52, 55, 135, and 165.

2. The set of two polypeptides according to claim 1, wherein:
the sequence of the N-terminal side fragment comprises the region between amino acid residues 19 and 59 of SEQ ID NO: 1 and the C-terminal side fragment comprises the region between amino acid residues 68 and 343 of SEQ ID NO: 1; or
the N-terminal side fragment comprises the region between amino acid residues 19 and 101 of SEQ ID NO: 1 and the C-terminal side fragment comprises the region between amino acid residues 111 and 343 of SEQ ID NO: 1.

3. The set of two polypeptides according to claim 1, wherein:
the N-terminal side fragment comprises the region between amino acid residues 19 and 59 of SEQ ID NO: 1 and the C-terminal side fragment comprises the region between amino acid residues 60 and 343 of SEQ ID NO: 1.

4. The set of two polypeptides according to claim 1, wherein:
the N-terminal side fragment comprises the region between amino acid residues 19 and 104 of SEQ ID NO: 1 and the C-terminal side fragment comprises the region between amino acid residues 106 and 343 of SEQ ID NO: 1.

5. The set of two polypeptides according to claim 1, wherein:
in one of the first and second proteins, at least one of the amino acid residues at positions 52 and 55 of SEQ ID NO: 2 is lysine, arginine, or histidine; and in the other of the first and second proteins, at least one of the amino acid residues at positions 52 and 55 of SEQ ID NO: 2 is aspartic acid, glutamic acid, or glycine.

6. The set of two polypeptides according to claim 1, wherein:
one of the first and second proteins is selected from the group consisting of: SEQ ID NO: 15 (pMag), SEQ ID NO: 16 (pMagHigh1), SEQ ID NO: 17 (pMagFast1), and SEQ ID NO: 18 (pMagFast2);
the other of the first and second proteins is selected from the group consisting of SEQ ID NO: 19 (nMag), SEQ ID NO: 20 (nMagHigh1), SEQ ID NO: 21 (nMagFast1), and SEQ ID NO: 22 (nMagFast2).

7. The set of two polypeptides according to claim 1, wherein:
the N-terminal side fragment and the C-terminal side fragment are each linked to their respective first and second proteins via a linker.

8. The set of two polypeptides according to claim 1, wherein:
one of the first and second proteins has a nuclear localization signal sequence linked, with or without a linker, to its C-terminal amino acid and/or
the other of the first and second proteins has a nuclear localization signal sequence linked, with or without a linker, to its N-terminal amino acid.

9. The set of two polypeptides according to claim 1, said first polypeptide, said second polypeptide, or both further comprise a 2A peptide sequence.

10. The set of two polypeptides according to claim 1, wherein:
one of the first and second polypeptides has, from its N-terminus to its C-terminus, the following amino acid sequences: the N-terminal side fragment linked to one of the first and second proteins linked to a first nuclear localization signal sequence linked to a portion of a first 2A peptide sequence; and
the other of the first and second polypeptides has, from its N-terminus to its C-terminus, the following amino acid sequences: a portion of a second 2A peptide sequence linked to a second nuclear localization signal sequence linked to the other of the first and second proteins linked to the C-terminal side fragment.

11. The set of two polypeptides according to claim 10, wherein each linkage is via a linker.

12. A nucleic acid which encodes one or both of the first and second polypeptides according to claim 1.

13. The nucleic acid according to claim 12, wherein the nucleic acid encodes the first and second polypeptides, in the following order, the N-terminal side fragment, one of the first and second proteins, a first nuclear localization signal sequence, a 2A peptide sequence, a second nuclear localization signal sequence, the other of the first and second proteins, and the C-terminal side fragment.

14. An expression vector comprising the nucleic acid as claimed in claim 12.

15. A Cre-loxP system comprising the nucleic acid as claimed in claim 12 and a nucleic acid having a loxP sequence or a loxP mutant sequence.

16. The Cre-loxP system according to claim 15, wherein:
the loxP mutant is selected from the group consisting of lox2722, lox66, lox71, JT15, and JTZ17.

* * * * *